US007138505B1

(12) United States Patent
Kuo et al.

(10) Patent No.: US 7,138,505 B1
(45) Date of Patent: Nov. 21, 2006

(54) FACTOR VIII:C NUCLEIC ACID MOLECULES

(75) Inventors: George Kuo, San Francisco, CA (US); Frank Masiarz, San Francisco, CA (US); Martha Truett, Oakland, CA (US); Pablo Valenzuela, San Francisco, CA (US); Mirella Ezban Rasmussen, Copenhagen (DK); Daniel Caput, San Francisco, CA (US); Rae Lyn Burke, San Francisco, CA (US); Carol Pachl, Oakland, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 07/569,376

(22) Filed: Aug. 13, 1990

Related U.S. Application Data

(60) Division of application No. 07/180,849, filed on Apr. 12, 1988, now abandoned, which is a continuation of application No. 06/757,095, filed on Jul. 19, 1985, now abandoned, which is a continuation-in-part of application No. 06/689,274, filed on Jan. 7, 1985, now Pat. No. 4,716,117, and a continuation-in-part of application No. 06/664,919, filed on Oct. 26, 1984, now abandoned, which is a continuation-in-part of application No. 06/570,062, filed on Jan. 12, 1984, now Pat. No. 5,004,804.

(51) Int. Cl.
*C07H 21/02* (2006.01)
*C07H 21/04* (2006.01)
*C12N 15/00* (2006.01)
*C12N 15/09* (2006.01)
*C12N 15/63* (2006.01)
*C12N 15/70* (2006.01)
*C12N 15/74* (2006.01)
*A01N 43/04* (2006.01)
*A61K 31/70* (2006.01)

(52) U.S. Cl. .................. 536/23.1; 424/93.1; 424/320.1; 514/44; 536/24.5; 536/23.4

(58) Field of Classification Search .............. 435/69.1, 435/69.6, 70.1, 91, 172.3, 320, 240.2, 252.33, 435/252.3; 530/383, 381; 536/27
See application file for complete search history.

(56) References Cited

U.S. PATENT DOCUMENTS

| | | | |
|---|---|---|---|
| 4,237,224 A | * | 12/1980 | Cohen et al. .................. 435/68 |
| 4,361,509 A | | 11/1982 | Zimmerman et al. |
| 4,363,877 A | * | 12/1982 | Goodman et al. ....... 435/320.1 |
| 4,394,443 A | * | 7/1983 | Weissman et al. ............. 435/6 |
| 4,419,446 A | | 12/1983 | Howley et al. |
| 4,649,132 A | | 3/1987 | Zimmerman et al. |
| 4,657,894 A | | 4/1987 | Zimmerman et al. |
| 4,716,117 A | | 12/1987 | Kuo et al. |
| 4,749,780 A | | 6/1988 | Andersson et al. |
| 4,757,006 A | | 7/1988 | Toole et al. |
| 5,618,788 A | | 4/1997 | Capon et al. |

FOREIGN PATENT DOCUMENTS

| | | |
|---|---|---|
| DK | 53519 | 3/1984 |
| EP | 083483 | 7/1983 |
| EP | 0120694 | 3/1984 |
| EP | 0123945 | 11/1984 |
| EP | 8404541 | 11/1984 |
| EP | 0150735 | 1/1985 |
| EP | 0143081 | 5/1985 |
| EP | 0182448 | 5/1985 |
| EP | 0157556 | 10/1985 |
| EP | 0160457 | 11/1985 |
| EP | 0182372 | 5/1986 |
| EP | 0232112 | 1/1987 |
| EP | 0197901 | 10/1987 |
| WO | WO 83/04029 | 11/1983 |
| WO | 8400594 | 2/1985 |
| WO | 8600774 | 10/1986 |

OTHER PUBLICATIONS

Fulcher et al., *Blood* (1983) 61:807.
Fulcher et al., *J. Clinical Invest.* (1985) 76:117-124.
Orr et al., *Mol. Genetics of Clotting Factors*, p. 54 in Thrombosis and Haemostasis, vol. 59, No. 1.
Rotblat et al., *Biochemistry* (1985) 24:4294-4300.
Toole et al., *Nature* (1984) 312:342-347.
Truett et al., *DNA* (1985) 4:333-349.
Vehar et al., *Nature* (1984) 312:337-342.
Wood et al., *Nature* (1984) 321:330-337.
Katz et al., *J. Immunol.* (1980) 124(2):819-824.
Andersson et al., *Proc. natl. Acad. Sci.* (1986) 83:2979-2983.

(Continued)

*Primary Examiner*—Joseph Woitach
*Assistant Examiner*—Robert M. Kelly
(74) *Attorney, Agent, or Firm*—Lisa M. Hemmendinger; Young J. Suh; Alisa A. Harbin

(57) ABSTRACT

Methods and compositions are provided for recombinant DNA production of Factor VIIIC and truncated derivatives thereof. Based on amino acid sequences, probes are developed for isolating messenger RNA, cDNA and/or chromosomal DNA encoding for Factor VIIIC. The Factor VIIIC gene in its entirety, a fragment thereof, or a cDNA is then used for expression of Factor VIIIC in a host.

The bacteriophage λFVIII23D containing the 14.43 kb EcoRI fragment was deposited at the A.T.C.C. on Jan. 4, 1984 and given Accession No. 40094. Also, the vector pSVF8-200 was deposited at the A.T.C.C. on Jul. 17, 1985 and given Accession No. 40190.

74 Claims, 14 Drawing Sheets

OTHER PUBLICATIONS

Austen, *British J. Hematology* (1979) 43:669-674.
Gitschier et al., *Nature* (1985) 312:326-330.
Bloom et al., *Nature* (1983) 303:474-475.
Burke et al., *J. Biol. Chem.* (1986) 261: 12574-12578.
Chan et al., *Chem. Abstracts* (1984) 100:214.
Choo et al., *Nature* (1983) 299:178-180.
Eaton et al., *Biochem.* (1986) 25(26):8343-8347.
Eaton et al., *Biochem.* (1986) 25:505-512.
Fass et al., *Blood* (1982) 59:594-600.
Fass et al., *Proc. Natl. Acad. Sci.* (1985) 82:1688:1691.
Fay et al., *Proc. Natl. Acad. Sci.* (1982) 79:7200-7204.
Fulcher et al., *Blood* (1984) 63(2):486-489.
Fulcher et al., *Chem. Abstr.* (1983) 98(21):450.
Orr et al., *J. Inter. Soc. Throm. Hemo.* (1985) 54(1):S321.
Peake et al., *Clin. Sci.* (1984) 67:561-567.
Rotblat et al., *Biological Abstracts* (1984) 77:4443.
Rotblat., *J. Lab. and Clin. Med.* (1983) 101:736-746.
Toole et al., *Proc. Natl. Acad. Sci.* (1986) 83:5939-5942.
Tuddenham et al., *J. Clin. Lab. Med.* (1979) 93:40-53.
Weinstein et al., *Proc. Natl. Acad. Sci.* (1981) 78:5137-5141.
Amended claim set filed in European patent application No. 91113267.8 (letter to European Patent Office dated Nov. 8, 1999).
Antakly et al., $\cdot_{2u}$-Globulin is present in the rat anterior pituitary, *Proc. Natl. Acad. Sci. U.S.A. 80*, 4000-02, Jul. 1983.
Benton & Davis, Screening •gt Recombinant Clones by Hybridization to Single Plaques in situ, *Science 196*, 180-82, Feb. 7, 1997.
Chirgwin et al., Isolation of Biologically Active Ribonucleic Acid from Sources Enriched in Ribonuclease, *Biochemistry 18*, 5294-99, 1979.
Choo et al., Molecular cloning of the gene for human anti-haemophilic factor IX, *Nature 299*, 178-80, Sep. 9, 1982.
Craig & Hall, Recombinant DNA technology: application to the characterization and expression of polypeptide hormones, in Williamson, ed., *Genetic Engineering 4*, 58-125, 1983.
Grunstein & Hogness, Colony hybridization: A method for the isolation of cloned DNAs that contain a specific gene, *Proc. Natl. Acad. Sci. U.S.A. 72*, 3961-65, Oct. 1975.
Holmes & Quigley, A Rapid Boiling Method for the Preparation of Bacterial Plasmids, *Anal. Biochem. 114*, 193-97, 1981.
Main and auxiliary requests filed in Eurpoean patent application No. 91113267.8 (letter to European Patent Office dated Sep. 21, 2000).
Maniatis et al., Molecular Cloning: A Laboratory Manual, Cold Spring Harbor Laboratory, 1982, Table of Contents.
Maxam & Gilbert, A new method for sequencing DNA, *Proc. Natl. Acad. Sci. U.S.A. 74*, 560-64, Feb. 1977.
Messing et al., Filamentous coliphage M13 as a cloning vehicle: Insertion of a HindII fragment of the *lac* regulatory region in M13 replicative form in vitro, *Proc. Natl. Acad. Sci. U.S.A. 74*, 3642-46, 1977.
Mesterovic et al., Detection of rennin mRNA in mouse kidney and submandibular gland by hybridization with rennin cDNA, *Endocrinology 113*, 1179-81, 1983.
Okayama & Berg, A cDNA Cloning Vector That Permits Expression of cDNA Inserts in Mammalian Cells, *Mol. Cell. Biol. 3*, 280-89, Feb. 1983.
Rigby et al., Labeling deoxyribonucleic acid to high specific activity in vitro by nick translation with DNA polymerase, *J. Mol. Biol. 113*, 237-51, 1977.
Southern, Detection of Specific Sequences Among DNA Fragments Separated by Gel Electrophoresis, *J. Mol. Biol. 98*, 503-17, 1975.
Toole et al., Molecular cloning of a cDNA encoding human antihaemophilic factor, *Nature 312*, 342-47, Nov. 22, 1984.
Truett et al., Characterization of the Polypeptide Composition of Human Factor VIII:C and the Nucleotide Sequence and Expression of the Human Kidney cDNA, *DNA 4*, 333-49, 1985.
Unterman et al., Cloning and sequence of several $\cdot_{2u}$-globulin cDNAs, *Proc. Natl. Acad. Sci. U.S.A. 78*, 3478-82, 1981.
Weinstock et al., Open reading frame expression vectors: A general method for antigen production in *Escherichia coli* using protein fusion to β-galactosidase, *Proc. Natl. Acad. Sci. U.S.A. 80*, 4432-36, Jul. 1983.
Yansura et al., Biosynthetic vaccine for foot-and-mouth disease, Advances in Genetic Technology: Molecular Genetics of Plants and Animals, pp. 479-93, 1983.
Marcelletti et al., *J. Immunol.* (1984) 133(6):2845-2851.
Marcelletti et al., *J. Immunol.* (1984) 133(6):2837-2844.
Zuraw et al., *J. Immunol.*(1981) 127(3):1169-1177.
Bloom et al., *Nature* (1983) 303:474-475.
Burke et al., *J. Biol. Chem.* (1986) 261: 12574-12578.
Chan et al., *Chem. Abstracts* (1984) 100:214.
Choo et al., *Nature* (1983) 299:178-180.
Eaton et al., *Biochem.* (1986) 25(26):8343-8347.
Eaton et al., *Biochem.* (1986) 25:505-512.
Fass et al., *Blood* (1982) 59:594-600.
Fass et al., *Proc. Natl. Acad. Sci.* (1985) 82:1688:1691.
Fay et al., *Proc. Natl. Acad. Sci.* (1982) 79:7200-7204.
Fulcher et al., *Blood* (1984) 63(2):486-489.
Fulcher et al., *Chem. Abstr.* (1983) 98(21):450.
Fulcher et al., *Proc. Natl. Acad. Sci.* (1982) 79:1648-1652.
Gitschier et al., *Nature* (1985) 315:427-430.
Hybritech Data Sheet (Catalogue #1432).
Jaye et al., *Nuc. Acids Res.* (1983) 11:2325-2335.
Kaufman et al., *Mol. and Cell. Bio.* (1982) 2:1304-1319.
Kuo et al., *Abstr. For XI Int. Congress of Throm. Haemostasis* (Jul. 1983) abstract No. 0818.
Kurachi et al., *Proc. Natl. Acad. Sci.* (1982) 79:6461-6464.
Lawn et al., *Scientific American* (Mar. 1986) pp. 48-54.
Lollar et al., *Biochemistry* (1985) 24:8056-8064.
Maddox, *Nature* (1983) 306:528.
Muller et al., *Blood* (1981) 58:1000-1006.
Muller et al., *Chem. Abstr.* (1982) 96(5):480.
Nordfang et al., *Thrombosis and Haemostasis* (1985) 54:586-590.

\* cited by examiner

FIG. 1A

```
  1 GCTTAGTGCTGAGCACATCCAGTGGGTAAAGTTCCTTAAAATGCTCTGCAAAGAAATTGG  F8-102
    CGAATCACGACTCGTGTAGGTCACCCATTTCAAGGAATTTTACGAGACGTTTCTTTAACC

61 GACTTTTCATTAAATCAGAAATTTTACTTTTTTCCCCTCCTGGGAGCTAAAGATATTTTA
    CTGAAAAGTAATTTAGTCTTTAAAATGAAAAAAGGGGAGGACCCTCGATTTCTATAAAAT

MetGlnIle
121 GAGAAGAATTAACCTTTTGCTTCTCCAGTTGAACATTTGTAGCAATAAGTCATGCAAATA
    CTCTTCTTAATTGGAAAACGAAGAGGTCAACTTGTAAACATCGTTATTCAGTACGTTTAT

GluLeuSerThrCysPhePheLeuCysLeuLeuArgPheCysPheSerAlaThrArgArg
181 GAGCTCTCCACCTGCTTCTTTCTGTGCCTTTTGCGATTCTGCTTTAGTGCCACCAGAAGA
    CTCGAGAGGTGGACGAAGAAAGACACGGAAAACGCTAAGACGAAATCACGGTGGTCTTCT 181 sac1, TyrTyrLeuGlyAlaValGluLeuSerTrpAspTyrMetGlnSerAspLeuGlyGluLeu
241 TACTACCTGGGTGCAGTGGAACTGTCATGGGACTATATGCAAAGTGATCTCGGTGAGCTG
    ATGATGGACCCACGTCACCTTGACAGTACCCTGATATACGTTTCACTAGAGCCACTCGAC ProValAspAlaArgPheProProArgValProLysSerPheProPheAsnThrSerVal
301 CCTGTGGACGCAAGATTTCCTCCTAGAGTGCCAAAATCTTTTCCATTCAACACCTCAGTC
    GGACACCTGCGTTCTAAAGGAGGATCTCACGGTTTTAGAAAAGGTAAGTTGTGGAGTCAG ValTyrLysLysThrLeuPheValGluPheThrAspHisLeuPheAsnIleAlaLysPro
361 GTGTACAAAAAGACTCTGTTTGTAGAATTCACGGATCACCTTTTCAACATCGCTAAGCCA
    CACATGTTTTTCTGAGACAAACATCTTAAGTGCCTAGTGGAAAAGTTGTAGCGATTCGGT 385 ecor1, ArgProProTrpMetGlyLeuLeuGlyProThrIleGlnAlaGluValTyrAspThrVal
421 AGGCCACCCTGGATGGGTCTGCTAGGTCCTACCATCCAGGCTGAGGTTTATGATACAGTG
    TCCGGTGGGACCTACCCAGACGATCCAGGATGGTAGGTCCGACTCCAAATACTATGTCAC ValIleThrLeuLysAsnMetAlaSerHisProValSerLeuHisAlaValGlyValSer
481 GTCATTACACTTAAGAACATGGCTTCCCATCCTGTCAGTCTTCATGCTGTTGGTGTATCC
    CAGTAATGTGAATTCTTGTACCGAAGGGTAGGACAGTCAGAAGTACGACAACCACATAGG 490 afl11, TyrTrpLysAlaSerGluGlyAlaGluTyrAspAspGlnThrSerGlnArgGluLysGlu
541 TACTGGAAAGCTTCTGAGGGAGCTGAATATGATGATCAGACCAGTCAAAGGGAGAAAGAA
    ATGACCTTTCGAAGACTCCCTCGACTTATACTACTAGTCTGGTCAGTTTCCCTCTTTCTT 548 hind111, 573 bc11, AspAspLysValPheProGlyGlySerHisThrTyrValTrpGlnValLeuLysGluAsn
601 GATGATAAAGTCTTCCCTGGTGGAAGCCATACATATGTCTGGCAGGTCCTGAAAGAGAAT
    CTACTATTTCAGAAGGGACCACCTTCGGTATGTATACAGACCGTCCAGGACTTTCTCTTA 632 nde1, GlyProMetAlaSerAspProLeuCysLeuThrTyrSerTyrLeuSerHisValAspLeu
661 GGTCCAATGGCCTCTGACCCACTGTGCCTTACCTACTCATATCTTTCTCATGTGGACCTG
    CCAGGTTACCGGAGACTGGGTGACACGGAATGGATGAGTATAGAAAGAGTACACCTGGAC
```

FIG. 1B

```
        ValLysAspLeuAsnSerGlyLeuIleGlyAlaLeuLeuValCysArgGluGlySerLeu
721     GTAAAAGACTTGAATTCAGGCCTCATTGGAGCCCTACTAGTATGTAGAGAAGGGAGTCTG
        CATTTTCTGAACTTAAGTCCGGAGTAACCTCGGGATGATCATACATCTCTTCCCTCAGAC 732 ecor1, 738 stu1, 756 spe1, 779 bal1, AlaLysGluLysThrGlnThrLeuHisLysPheIleLeuLeuPheAlaValPheAspGlu
781     GCCAAGGAAAAGACACAGACCTTGCACAAATTTATACTACTTTTTGCTGTATTTGATGAA
        CGGTTCCTTTTCTGTGTCTGGAACGTGTTTAAATATGATGAAAAACGACATAAACTACTT GlyLysSerTrpHisSerGluThrLysAsnSerLeuMetGlnAspArgAspAlaAlaSer
841     GGGAAAAGTTGGCACTCAGAAACAAAGAACTCCTTGATGCAGGATAGGGATGCTGCATCT
        CCCTTTTCAACCGTGAGTCTTTGTTTCTTGAGGAACTACGTCCTATCCCTACGACGTAGA AlaArgAlaTrpProLysMetHisThrValAsnGlyTyrValAsnArgSerLeuProGly
901     GCTCGGGCCTGGCCTAAAATGCACACAGTCAATGGTTATGTAAACAGGTCTCTGCCAGGT
        CGAGCCCGGACCGGATTTTACGTGTGTCAGTTACCAATACATTTGTCCAGAGACGGTCCA LeuIleGlyCysHisArgLysSerValTyrTrpHisValIleGlyMetGlyThrThrPro
961     CTGATTGGATGCCACAGGAAATCAGTCTATTGGCATGTGATTGGAATGGGCACCACTCCT
        GACTAACCTACGGTGTCCTTTAGTCAGATAACCGTACACTAACCTTACCCGTGGTGAGGA GluValHisSerIlePheLeuGluGlyHisThrPheLeuValArgAsnHisArgGlnAla
1021    GAAGTGCACTCAATATTCCTCGAAGGTCACACATTTCTTGTGAGGAACCATCGCCAGGCG
        CTTCACGTGAGTTATAAGGAGCTTCCAGTGTGTAAAGAACACTCCTTGGTAGCGGTCCGC 1032 ssp1, SerLeuGluIleSerProIleThrPheLeuThrAlaGlnThrLeuLeuMetAspLeuGly
1081    TCCTTGGAAATCTCGCCAATAACTTTCCTTACTGCTCAAACACTCTTGATGGACCTTGGA
        AGGAACCTTTAGAGCGGTTATTGAAAGGAATGACGAGTTTGTGAGAACTACCTGGAACCT GlnPheLeuLeuPheCysHisIleSerSerHisGlnHisAspGlyMetGluAlaTyrVal
1141    CAGTTTCTACTGTTTTGTCATATCTCTTCCCACCAACATGATGGCATGGAAGCTTATGTC
        GTCAAAGATGACAAAACAGTATAGAGAAGGGTGGTTGTACTACCGTACCTTCGAATACAG 1173 bstXI, 1190 hind111, LysValAspSerCysProGluGluProGlnLeuArgMetLysAsnAsnGluGluAlaGlu
1201    AAAGTAGACAGCTGTCCAGAGGAACCCCAACTACGAATGAAAAATAATGAAGAAGCGGAA
        TTTCATCTGTCGACAGGTCTCCTTGGGGTTGATGCTTACTTTTTATTACTTCTTCGCCTT 1209 pvu11, AspTyrAspAspAspLeuThrAspSerGluMetAspValValArgPheAspAspAspAsn
1261    GACTATGATGATGATCTTACTGATTCTGAAATGGATGTGGTCAGGTTTGATGATGACAAC
        CTGATACTACTACTAGAATGACTAAGACTTTACCTACACCAGTCCAAACTACTACTGTTG SerProSerPheIleGlnIleArgSerValAlaLysLysHisProLysThrTrpValHis
1321    TCTCCTTCCTTTATCCAAATTCGCTCAGTTGCCAAGAAGCATCCTAAAACTTGGGTACAT
        AGAGGAAGGAAATAGGTTTAAGCGAGTCAACGGTTCTTCGTAGGATTTTGAACCCATGTA TyrIleAlaAlaGluGluGluAspTrpAspTyrAlaProLeuValLeuAlaProAspAsp
1381    TACATTGCTGCTGAAGAGGAGGACTGGGACTATGCTCCCTTAGTCCTCGCCCCCGATGAC
        ATGTAACGACGACTTCTCCTCCTGACCCTGATACGAGGGAATCAGGAGCGGGGGCTACTG
```

FIG. 1C

```
       ArgSerTyrLysSerGlnTyrLeuAsnAsnGlyProGlnArgIleGlyArgLysTyrLys
1441   AGAAGTTATAAAAGTCAATATTTGAACAATGGCCCTCAGCGGATTGGTAGGAAGTACAAA
       TCTTCAATATTTTCAGTTATAAACTTGTTACCGGGAGTCGCCTAACCATCCTTCATGTTT 1457 sspl, LysValArgPheMetAlaTyrThrAspGluThrPheLysThrArgGluAlaIleGlnHis
1501   AAAGTCCGATTTATGGCATACACAGATGAAACCTTTAAGACTCGTGAAGCTATTCAGCAT
       TTTCAGGCTAAATACCGTATGTGTCTACTTTGGAAATTCTGAGCACTTCGATAAGTCGTA 1546 xmnl, GluSerGlyIleLeuGlyProLeuLeuTyrGlyGluValGlyAspThrLeuLeuIleIle
1561   GAATCAGGAATCTTGGGACCTTTACTTTATGGGGAAGTTGGAGACACACTGTTGATTATA
       CTTAGTCCTTAGAACCCTGGAAATGAAATACCCCTTCAACCTCTGTGTGACAACTAATAT PheLysAsnGlnAlaSerArgProTyrAsnIleTyrProHisGlyIleThrAspValArg
1621   TTTAAGAATCAAGCAAGCAGACCATATAACATCTACCCTCACGGAATCACTGATGTCCGT
       AAATTCTTAGTTCGTTCGTCTGGTATATTGTAGATGGGAGTGCCTTAGTGACTACAGGCA ProLeuTyrSerArgArgLeuProLysGlyValLysHisLeuLysAspPheProIleLeu
1681   CCTTTGTATTCAAGGAGATTACCAAAAGGTGTAAAACATTTGAAGGATTTTCCAATTCTG
       GGAAACATAAGTTCCTCTAATGGTTTTCCACATTTTGTAAACTTCCTAAAAGGTTAAGAC ProGlyGluIlePheLysTyrLysTrpThrValThrValGluAspGlyProThrLysSer
1741   CCAGGAGAAATATTCAAATATAAATGGACAGTGACTGTAGAAGATGGGCCAACTAAATCA
       GGTCCTCTTTATAAGTTTATATTTACCTGTCACTGACATCTTCTACCCGGTTGATTTAGT 1749 sspl, AspProArgCysLeuThrArgTyrTyrSerSerPheValAsnMetGluArgAspLeuAla
1801   GATCCTCGGTGCCTGACCCGCTATTACTCTAGTTTCGTTAATATGGAGAGAGATCTAGCT
       CTAGGAGCCACGGACTGGGCGATAATGAGATCAAAGCAATTATACCTCTCTCTAGATCGA 1851 bgl11, SerGlyLeuIleGlyProLeuLeuIleCysTyrLysGluSerValAspGlnArgGlyAsn
1861   TCAGGACTCATTGGCCCTCTCCTCATCTGCTACAAAGAATCTGTAGATCAAAGAGGAAAC
       AGTCCTGAGTAACCGGGAGAGGAGTAGACGATGTTTCTTAGACATCTAGTTTCTCCTTTG GlnIleMetSerAspLysArgAsnValIleLeuPheSerValPheAspGluAsnArgSer
1921   CAGATAATGTCAGACAAGAGGAATGTCATCCTGTTTTCTGTATTTGATGAGAACCGAAGC
       GTCTATTACAGTCTGTTCTCCTTACAGTAGGACAAAAGACATAAACTACTCTTGGCTTCG TrpTyrLeuThrGluAsnIleGlnArgPheLeuProAsnProAlaGlyValGlnLeuGlu
1981   TGGTACCTCACAGAGAATATACAACGCTTTCTCCCCAATCCAGCTGGAGTGCAGCTTGAG
       ACCATGGAGTGTCTCTTATATGTTGCGAAAGAGGGGTTAGGTCGACCTCACGTCGAACTC 1982 kpnl, 2021 pvull, 2040 bamhl, AspProGluPheGlnAlaSerAsnIleMetHisSerIleAsnGlyTyrValPheAspSer
2041   GATCCAGAGTTCCAAGCCTCCAACATCATGCACAGCATCAATGGCTATGTTTTTGATAGT
       CTAGGTCTCAAGGTTCGGAGGTTGTAGTACGTGTCGTAGTTACCGATACAAAAACTATCA LeuGlnLeuSerValCysLeuHisGluValAlaTyrTrpTyrIleLeuSerIleGlyAla
2101   TTGCAGTTGTCAGTTTGTTTGCATGAGGTGGCATACTGGTACATTCTAAGCATTGGAGCA
       AACGTCAACAGTCAAACAAACGTACTCCACCGTATGACCATGTAAGATTCGTAACCTCGT
```

FIG. 1D

```
      GlnThrAspPheLeuSerValPhePheSerGlyTyrThrPheLysHisLysMetValTyr
2161  CAGACTGACTTCCTTTCTGTCTTCTTCTCTGGATATACCTTCAAACACAAAATGGTCTAT
      GTCTGACTGAAGGAAAGACAGAAGAAGAGACCTATATGGAAGTTTGTGTTTTACCAGATA

GluAspThrLeuThrLeuPheProPheSerGlyGluThrValPheMetSerMetGluAsn
2221  GAAGACACACTCACCCTATTCCCATTCTCAGGAGAAACTGTCTTCATGTCGATGGAAAAC
      CTTCTGTGTGAGTGGGATAAGGGTAAGAGTCCTCTTTGACAGAAGTACAGCTACCTTTTG

ProGlyLeuTrpIleLeuGlyCysHisAsnSerAspPheArgAsnArgGlyMetThrAla
2281  CCAGGTCTATGGATTCTGGGGTGCCACAACTCAGACTTTCGGAACAGAGGCATGACCGCC
      GGTCCAGATACCTAAGACCCCACGGTGTTGAGTCTGAAAGCCTTGTCTCCGTACTGGCGG 2281 bstXI, LeuLeuLysValSerSerCysAspLysAsnThrGlyAspTyrTyrGluAspSerTyrGlu
2341  TTACTGAAGGTTTCTAGTTGTGACAAGAACACTGGTGATTATTACGAGGACAGTTATGAA
      AATGACTTCCAAAGATCAACACTGTTCTTGTGACCACTAATAATGCTCCTGTCAATACTT AspIleSerAlaTyrLeuLeuSerLysAsnAsnAlaIleGluProArgSerPheSerGln
2401  GATATTTCAGCATACTTGCTGAGTAAAAACAATGCCATTGAACCAAGAAGCTTCTCCCAG
      CTATAAAGTCGTATGAACGACTCATTTTTGTTACGGTAACTTGGTTCTTCGAAGAGGGTC 2448 hind111, 2460 ecor1, AsnSerArgHisProSerThrArgGlnLysGlnPheAsnAlaThrThrIleProGluAsn
2461  AATTCAAGACACCCTAGCACTAGGCAAAAGCAATTTAATGCCACCACAATTCCAGAAAAT
      TTAAGTTCTGTGGGATCGTGATCCGTTTTCGTTAAATTACGGTGGTGTTAAGGTCTTTTA AspIleGluLysThrAspProTrpPheAlaHisArgThrProMetProLysIleGlnAsn
2521  GACATAGAGAAGACTGACCCTTGGTTTGCACACAGAACACCTATGCCTAAAATACAAAAT
      CTGTATCTCTTCTGACTGGGAACCAAACGTGTGTCTTGTGGATACGGATTTTATGTTTTA ValSerSerSerAspLeuLeuMetLeuLeuArgGlnSerProThrProHisGlyLeuSer
2581  GTCTCCTCTAGTGATTTGTTGATGCTCTTGCGACAGAGTCCTACTCCACATGGGCTATCC
      CAGAGGAGATCACTAAACAACTACGAGAACGCTGTCTCAGGATGAGGTGTACCCGATAGG 2612 tthIII1, LeuSerAspLeuGlnGluAlaLysTyrGluThrPheSerAspAspProSerProGlyAla
2641  TTATCTGATCTCCAAGAAGCCAAATATGAGACTTTTTCTGATGATCCATCACCTGGAGCA
      AATAGACTAGAGGTTCTTCGGTTTATACTCTGAAAAAGACTACTAGGTAGTGGACCTCGT IleAspSerAsnAsnSerLeuSerGluMetThrHisPheArgProGlnLeuHisHisSer
2701  ATAGACAGTAATAACAGCCTGTCTGAAATGACACACTTCAGGCCACAGCTCCATCACAGT
      TATCTGTCATTATTGTCGGACAGACTTTACTGTGTGAAGTCCGGTGTCGAGGTAGTGTCA 2751 bstXI, GlyAspMetValPheThrProGluSerGlyLeuGlnLeuArgLeuAsnGluLysLeuGly
2761  GGGGACATGGTATTTACCCCTGAGTCAGGCCTCCAATTAAGATTAAATGAGAAACTGGGG
      CCCCTGTACCATAAATGGGGACTCAGTCCGGAGGTTAATTCTAATTTACTCTTTGACCCC 2780 tthIII1, 2787 stu1, ThrThrAlaAlaThrGluLeuLysLysLeuAspPheLysValSerSerThrSerAsnAsn
2821  ACAACTGCAGCAACAGAGTTGAAGAAACTTGATTTCAAAGTTTCTAGTACATCAAATAAT
      TGTTGACGTCGTTGTCTCAACTTCTTTGAACTAAAGTTTCAAAGATCATGTAGTTTATTA 2825 pst1,
```

FIG. 1E

```
        LeuIleSerThrIleProSerAspAsnLeuAlaAlaGlyThrAspAsnThrSerSerLeu
2881    CTGATTTCAACAATTCCATCAGACAATTTGGCAGCAGGTACTGATAATACAAGTTCCTTA
        GACTAAAGTTGTTAAGGTAGTCTGTTAAACCGTCGTCCATGACTATTATGTTCAAGGAAT 2936 mstII, GlyProProSerMetProValHisTyrAspSerGlnLeuAspThrThrLeuPheGlyLys
2941    GGACCCCCAAGTATGCCAGTTCATTATGATAGTCAATTAGATACCACTCTATTTGGCAAA
        CCTGGGGGTTCATACGGTCAAGTAATACTATCAGTTAATCTATGGTGAGATAAACCGTTT LysSerSerProLeuThrGluSerGlyGlyProLeuSerLeuSerGluGluAsnAsnAsp
3001    AAGTCATCTCCCCTTACTGAGTCTGGTGGACCTCTGAGCTTGAGTGAAGAAAATAATGAT
        TTCAGTAGAGGGGAATGACTCAGACCACCTGGAGACTCGAACTCACTTCTTTTATTACTA SerLysLeuLeuGluSerGlyLeuMetAsnSerGlnGluSerSerTrpGlyLysAsnVal
3061    TCAAAGTTGTTAGAATCAGGTTTAATGAATAGCCAAGAAAGTTCATGGGGAAAAAATGTA
        AGTTTCAACAATCTTAGTCCAAATTACTTATCGGTTCTTTCAAGTACCCCTTTTTTACAT SerSerThrGluSerGlyArgLeuPheLysGlyLysArgAlaHisGlyProAlaLeuLeu
3121    TCGTCAACAGAGAGTGGTAGGTTATTTAAAGGGAAAAGAGCTCATGGACCTGCTTTGTTG
        AGCAGTTGTCTCTCACCATCCAATAAATTTCCCTTTTCTCGAGTACCTGGACGAAACAAC 3145 aha1II, 3158 sacI, ThrLysAspAsnAlaLeuPheLysValSerIleSerLeuLeuLysThrAsnLysThrSer
3181    ACTAAAGATAATGCCTTATTCAAAGTTAGCATCTCTTTGTTAAAGACAAACAAAACTTCC
        TGATTTCTATTACGGAATAAGTTTCAATCGTAGAGAAACAATTTCTGTTTGTTTTGAAGG AsnAsnSerAlaThrAsnArgLysThrHisIleAspGlyProSerLeuLeuIleGluAsn
3241    AATAATTCAGCAACTAATAGAAAGACTCACATTGATGGCCCATCATTATTAATTGAGAAT
        TTATTAAGTCGTTGATTATCTTTCTGAGTGTAACTACCGGGTAGTAATAATTAACTCTTA SerProSerValTrpGlnAsnIleLeuGluSerAspThrGluPheLysLysValThrPro
3301    AGTCCATCAGTCTGGCAAAATATATTAGAAAGTGACACTGAGTTTAAAAAAGTGACACCT
        TCAGGTAGTCAGACCGTTTTATATAATCTTTCACTGTGACTCAAATTTTTTCACTGTGGA 3304 bstXI, 3343 aha1II, LeuIleHisAspArgMetLeuMetAspLysAsnAlaThrAlaLeuArgLeuAsnHisMet
3361    TTGATTCATGACAGAATGCTTATGGACAAAAATGCTACAGCTTTGAGGCTAAATCATATG
        AACTAAGTACTGTCTTACGAATACCTGTTTTTACGATGTCGAAACTCCGATTTAGTATAC 3374 bsmI, 3415 ndeI, SerAsnLysThrThrSerSerLysAsnMetGluMetValGlnGlnLysLysGluGlyPro
3421    TCAAATAAAACTACTTCATCAAAAAACATGGAAATGGTCCAACAGAAAAAGAGGGCCCC
        AGTTTATTTTGATGAAGTAGTTTTTTGTACCTTTACCAGGTTGTCTTTTTTCTCCCGGGG 3474 apaI, IleProProAspAlaGlnAsnProAspMetSerPhePheLysMetLeuPheLeuProGlu
3481    ATTCCACCAGATGCACAAAATCCAGATATGTCGTTCTTTAAGATGCTATTCTTGCCAGAA
        TAAGGTGGTCTACGTGTTTTAGGTCTATACAGCAAGAAATTCTACGATAAGAACGGTCTT SerAlaArgTrpIleGlnArgThrHisGlyLysAsnSerLeuAsnSerGlyGlnGlyPro
3541    TCAGCAAGGTGGATACAAAGGACTCATGGAAAGAACTCTCTGAACTCTGGGCAAGGCCCC
        AGTCGTTCCACCTATGTTTCCTGAGTACCTTTCTTGAGAGACTTGAGACCCGTTCCGGGG
```

FIG. 1F

```
          SerProLysGlnLeuValSerLeuGlyProGluLysSerValGluGlyGlnAsnPheLeu
3601      AGTCCAAAGCAATTAGTATCCTTAGGACCAGAAAAATCTGTGGAAGGTCAGAATTTCTTG
          TCAGGTTTCGTTAATCATAGGAATCCTGGTCTTTTTAGACACCTTCCAGTCTTAAAGAAC 3620 mstII, SerGluLysAsnLysValValValGlyLysGlyGluPheThrLysAspValGlyLeuLys
3661      TCTGAGAAAAACAAAGTGGTAGTAGGAAAGGGTGAATTTACAAAGGACGTAGGACTCAAA
          AGACTCTTTTTGTTTCACCATCATCCTTTCCCACTTAAATGTTTCCTGCATCCTGAGTTT GluMetValPheProSerSerArgAsnLeuPheLeuThrAsnLeuAspAsnLeuHisGlu
3721      GAGATGGTTTTTCCAAGCAGCAGAAACCTATTTCTTACTAACTTGGATAATTTACATGAA
          CTCTACCAAAAAGGTTCGTCGTCTTTGGATAAAGAATGATTGAACCTATTAAATGTACTT AsnAsnThrHisAsnGlnGluLysLysIleGlnGluGluIleGluLysLysGluThrLeu
3781      AATAATACACACAATCAAGAAAAAAAAATTCAGGAAGAAATAGAAAAGAAGGAAACATTA
          TTATTATGTGTGTTAGTTCTTTTTTTTAAGTCCTTCTTTATCTTTTCTTCCTTTGTAAT IleGlnGluAsnValValLeuProGlnIleHisThrValThrGlyThrLysAsnPheMet
3841      ATCCAAGAGAATGTAGTTTTGCCTCAGATACATACAGTGACTGGCACTAAGAATTTCATG
          TAGGTTCTCTTACATCAAAACGGAGTCTATGTATGTCACTGACCGTGATTCTTAAAGTAC LysAsnLeuPheLeuLeuSerThrArgGlnAsnValGluGlySerTyrAspGlyAlaTyr
3901      AAGAACCTTTTCTTACTGAGCACTAGGCAAAATGTAGAAGGTTCATATGACGGGGCATAT
          TTCTTGGAAAAGAATGACTCGTGATCCGTTTTACATCTTCCAAGTATACTGCCCCGTATA 3903 xmn1, 3944 nde1, 3956 nde1, AlaProValLeuGlnAspPheArgSerLeuAsnAspSerThrAsnArgThrLysLysHis
3961      GCTCCAGTACTTCAAGATTTTAGGTCATTAAATGATTCAACAAATAGAACAAAGAAACAC
          CGAGGTCATGAAGTTCTAAAATCCAGTAATTTACTAAGTTGTTTATCTTGTTTCTTTGTG 3966 sca1, ThrAlaHisPheSerLysLysGlyGluGluGluAsnLeuGluGlyLeuGlyAsnGlnThr
4021      ACAGCTCATTTCTCAAAAAAGGGGAGGAAGAAAAACTTGGAAGGCTTGGGAAATCAAACC
          TGTCGAGTAAAGAGTTTTTTTCCCCTCCTTCTTTTGAACCTTCCGAACCCTTTAGTTTGG LysGlnIleValGluLysTyrAlaCysThrThrArgIleSerProAsnThrSerGlnGln
4081      AAGCAAATTGTAGAGAAATATGCATGCACCACAAGGATATCTCCTAATACAAGCCAGCAG
          TTCGTTTAACATCTCTTTATACGTACGTGGTGTTCCTATAGAGGATTATGTTCGGTCGTC 4100 ava3, 4102 sph1, 4116 ecor5, AsnPheValThrGlnArgSerLysArgAlaLeuLysGlnPheArgLeuProLeuGluGlu    F8-100
4141      AATTTTGTCACGCAACGTAGTAAGAGAGCTTTGAAACAATTCAGACTCCCACTAGAAGAA
          TTAAAACAGTGCGTTGCATCATTCTCTCGAAACTTTGTTAAGTCTGAGGGTGATCTTCTT 4173 xmn1, ThrGluLeuGluLysArgIleIleValAspAspThrSerThrGlnTrpSerLysAsnMet
4201      ACAGAACTTGAAAAAAGGATAATTGTGGATGACACCTCAACCCAGTGGTCCAAAAACATG
          TGTCTTGAACTTTTTTCCTATTAACACCTACTGTGGAGTTGGGTCACCAGGTTTTTGTAC LysHisLeuThrProSerThrLeuThrGlnIleAspTyrAsnGluLysGluLysGlyAla
4261      AAACATTTGACCCCGAGCACCCTCACACAGATAGACTACAATGAAGGAGAAAGGGGCC
          TTTGTAAACTGGGGCTCGTGGGAGTGTGTCTATCTGATGTTACTCTTCCTCTTTCCCCGG
```

FIG. 1G

```
        IleThrGlnSerProLeuSerAspCysLeuThrArgSerHisSerIleProGlnAlaAsn
4321    ATTACTCAGTCTCCCTTATCAGATTGCCTTACGAGGAGTCATAGCATCCCTCAAGCAAAT
        TAATGAGTCAGAGGGAATAGTCTAACGGAATGCTCCTCAGTATCGTAGGGAGTTCGTTTA
        ━━━━━━━━━━━━━━━━━━━━━━━━━━━━━━━━━━━━━━━━━━━━━━━━━━━━━━━━━━━━
        INTERNAL PRIMER FOR cDNA SYNTHESIS

ArgSerProLeuProIleAlaLysValSerSerPheProSerIleArgProIleTyrLeu
4381    AGATCTCCATTACCCATTGCAAAGGTATCATCATTTCCATCTATTAGACCTATATATCTG
        TCTAGAGGTAATGGGTAACGTTTCCATAGTAGTAAAGGTAGATAATCTGGATATATAGAC
                                                    ^
        4381 bglII, ThrArgValLeuPheGlnAspAsnSerSerHisLeuProAlaAlaSerTyrArgLysLys
4441    ACCAGGGTCCTATTCCAAGACAACTCTTCTCATCTTCCAGCAGCATCTTATAGAAAGAAA
        TGGTCCCAGGATAAGGTTCTGTTGAGAAGAGTAGAAGGTCGTCGTAGAATATCTTTCTTT AspSerGlyValGlnGluSerSerHisPheLeuGlnGlyAlaLysLysAsnAsnLeuSer
4501    GATTCTGGGGTCCAAGAAAGCAGTCATTTCTTACAAGGAGCCAAAAAAAATAACCTTTCT
        CTAAGACCCCAGGTTCTTTCGTCAGTAAAGAATGTTCCTCGGTTTTTTTATTGGAAAGA LeuAlaIleLeuThrLeuGluMetThrGlyAspGlnArgGluValGlySerLeuGlyThr
4561    TTAGCCATTCTAACCTTGGAGATGACTGGTGATCAAAGAGAGGTTGGCTCCCTGGGGACA
        AATCGGTAAGATTGGAACCTCTACTGACCACTAGTTTCTCTCCAACCGAGGGACCCCTGT
                                     ^
        4590 bclI, SerAlaThrAsnSerValThrTyrLysLysValGluAsnThrValLeuProLysProAsp
4621    AGTGCCACAAATTCAGTCACATACAAGAAAGTTGAGAACACTGTTCTCCCGAAACCAGAC
        TCACGGTGTTTAAGTCAGTGTATGTTCTTTCAACTCTTGTGACAAGAGGGCTTTGGTCTG LeuProLysThrSerGlyLysValGluLeuLeuProLysValHisIleTyrGlnLysAsp
4681    TTGCCCAAAACATCTGGCAAAGTTGAATTGCTTCCAAAAGTTCACATTTATCAGAAGGAC
        AACGGGTTTTGTAGACCGTTTCAACTTAACGAAGGTTTTCAAGTGTAAATAGTCTTCCTG
                                    ^
        4705 xmnI, LeuPheProThrGluThrSerAsnGlySerProGlyHisLeuAspLeuValGluGlySer
4741    CTATTCCCTACGGAAACTAGCAATGGGTCTCCTGGCCATCTGGATCTCGTGGAAGGGAGC
        GATAAGGGATGCCTTTGATCGTTACCCAGAGGACCGGTAGACCTAGAGCACCTTCCCTCG
                                              ^
        4773 balI, LeuLeuGlnGlyThrGluGlyAlaIleLysTrpAsnGluAlaAsnArgProGlyLysVal
4801    CTTCTTCAGGGAACAGAGGGAGCGATTAAGTGGAATGAAGCAAACAGACCTGGAAAAGTT
        GAAGAAGTCCCTTGTCTCCCTCGCTAATTCACCTTACTTCGTTTGTCTGGACCTTTTCAA ProPheLeuArgValAlaThrGluSerSerAlaLysThrProSerLysLeuLeuAspPro
4861    CCCTTTCTGAGAGTAGCAACAGAAAGCTCTGCAAAGACTCCCTCCAAGCTATTGGATCCT
        GGGAAAGACTCTCATCGTTGTCTTTCGAGACGTTTCTGAGGGAGGTTCGATAACCTAGGA
                                                            ^
        4904 bstXI, 4914 bamhI, LeuAlaTrpAspAsnHisTyrGlyThrGlnIleProLysGluGluTrpLysSerGlnGlu
4921    CTTGCTTGGGATAACCACTATGGTACTCAGATACCAAAAGAAGAGTGGAAATCCCAAGAG
        GAACGAACCCTATTGGTGATACCATGAGTCTATGGTTTTCTTCTCACCTTTAGGGTTCTC LysSerProGluLysThrAlaPheLysLysLysAspThrIleLeuSerLeuAsnAlaCys
4981    AAGTCACCAGAAAAAACAGCTTTTAAGAAAAAGGATACCATTTTGTCCCTGAACGCTTGT
        TTCAGTGGTCTTTTTTGTCGAAAATTCTTTTTCCTATGGTAAAACAGGGACTTGCGAACA
```

FIG. 1H

```
        GluSerAsnHisAlaIleAlaAlaIleAsnGluGlyGlnAsnLysProGluIleGluVal
5041    GAAAGCAATCATGCAATAGCAGCAATAAATGAGGGACAAAATAAGCCCGAAATAGAAGTC
        CTTTCGTTAGTACGTTATCGTCGTTATTTACTCCCTGTTTTATTCGGGCTTTATCTTCAG

ThrTrpAlaLysGlnGlyArgThrGluArgLeuCysSerGlnAsnProProValLeuLys
5101    ACCTGGGCAAAGCAAGGTAGGACTGAAAGGCTGTGCTCTCAAAACCCACCAGTCTTGAAA
        TGGACCCGTTTCGTTCCATCCTGACTTTCCGACACGAGAGTTTTGGGTGGTCAGAACTTT

ArgHisGlnArgGluIleThrArgThrThrLeuGlnSerAspGlnGluGluIleAspTyr
5161    CGCCATCAACGGGAAATAACTCGTACTACTCTTCAGTCAGATCAAGAGGAAATTGACTAT
        GCGGTAGTTGCCCTTTATTGAGCATGATGAGAAGTCAGTCTAGTTCTCCTTTAACTGATA

AspAspThrIleSerValGluMetLysLysGluAspPheAspIleTyrAspGluAspGlu
5221    GATGATACCATATCAGTTGAAATGAAGAAGGAAGATTTTGACATTTATGATGAGGATGAA
        CTACTATGGTATAGTCAACTTTACTTCTTCCTTCTAAAACTGTAAATACTACTCCTACTT

AsnGlnSerProArgSerPheGlnLysLysThrArgHisTyrPheIleAlaAlaValGlu
5281    AATCAGAGCCCCCGCAGCTTTCAAAAGAAAACACGACACTATTTTATTGCTGCAGTGGAG
        TTAGTCTCGGGGGCGTCGAAAGTTTTCTTTTGTGCTGTGATAAAATAACGACGTCACCTC 5330 pst1, ArgLeuTrpAspTyrGlyMetSerSerSerProHisValLeuArgAsnArgAlaGlnSer
5341    AGGCTCTGGGATTATGGGATGAGTAGCTCCCCACATGTTCTAAGAAACAGGGCTCAGAGT
        TCCGAGACCCTAATACCCTACTCATCGAGGGGTGTACAAGATTCTTTGTCCCGAGTCTCA GlySerValProGlnPheLysLysValValPheGlnGluPheThrAspGlySerPheThr
5401    GGCAGTGTCCCTCAGTTCAAGAAAGTTGTTTTCCAGGAATTTACTGATGGCTCCTTTACT
        CCGTCACAGGGAGTCAAGTTCTTTCAACAAAAGGTCCTTAAATGACTACCGAGGAAATGA GlnProLeuTyrArgGlyGluLeuAsnGluHisLeuGlyLeuLeuGlyProTyrIleArg
5461    CAGCCCTTATACCGTGGAGAACTAAATGAACATTTGGGACTCCTGGGGCCATATATAAGA
        GTCGGGAATATGGCACCTCTTGATTTACTTGTAAACCCTGAGGACCCCGGTATATATTCT AlaGluValGluAspAsnIleMetValThrPheArgAsnGlnAlaSerArgProTyrSer
5521    GCAGAAGTTGAAGATAATATCATGGTAACTTTCAGAAATCAGGCCTCTCGTCCCTATTCC
        CGTCTTCAACTTCTATTATAGTACCATTGAAAGTCTTTAGTCCGGAGAGCAGGGATAAGG 5561 stu1, PheTyrSerSerLeuIleSerTyrGluGluAspGlnArgGlnGlyAlaGluProArgLys
5581    TTCTATTCTAGCCTTATTTCTTATGAGGAAGATCAGAGGCAAGGAGCAGAACCTAGAAAA
        AAGATAAGATCGGAATAAAGAATACTCCTTCTAGTCTCCGTTCCTCGTCTTGGATCTTTT AsnPheValLysProAsnGluThrLysThrTyrPheTrpLysValGlnHisHisMetAla
5641    AACTTTGTCAAGCCTAATGAAACCAAAACTTACTTTTGGAAAGTGCAACATCATATGGCA
        TTGAAACAGTTCGGATTACTTTGGTTTTGAATGAAAACCTTTCACGTTGTAGTATACCGT 5692 nde1, ProThrLysAspGluPheAspCysLysAlaTrpAlaTyrPheSerAspValAspLeuGlu
5701    CCCACTAAAGATGAGTTTGACTGCAAAGCCTGGGCTTATTTCTCTGATGTTGACCTGGAA
        GGGTGATTTCTACTCAAACTGACGTTTCGGACCCGAATAAAGAGACTACAACTGGACCTT LysAspValHisSerGlyLeuIleGlyProLeuLeuValCysHisThrAsnThrLeuAsn
5761    AAAGATGTGCACTCAGGCCTGATTGGACCCCTTCTGGTCTGCCACACTAACACACTGAAC
        TTTCTACACGTGAGTCCGGACTAACCTGGGGAAGACCAGACGGTGTGATTGTGTGACTTG 5775 stu1,
```

FIG. 1I

```
              ProAlaHisGlyArgGlnValThrValGlnGluPheAlaLeuPhePheThrIlePheAsp
       5821   CCTGCTCATGGGAGACAAGTGACAGTACAGGAATTTGCTCTGTTTTTCACCATCTTTGAT
              GGACGAGTACCCTCTGTTCACTGTCATGTCCTTAAACGAGACAAAAAGTGGTAGAAACTA

GluThrLysSerTrpTyrPheThrGluAsnMetGluArgAsnCysArgAlaProCysAsn
       5881   GAGACCAAAAGCTGGTACTTCACTGAAAATATGGAAAGAAACTGCAGGGCTCCCTGCAAT
              CTCTGGTTTTCGACCATGAAGTGACTTTTATACCTTTCTTTGACGTCCCGAGGGACGTTA 5922 pst1, IleGlnMetGluAspProThrPheLysGluAsnTyrArgPheHisAlaIleAsnGlyTyr
       5941   ATCCAGATGGAAGATCCCACTTTTAAAGAGAATTATCGCTTCCATGCAATCAATGGCTAC
              TAGGTCTACCTTCTAGGGTGAAAATTTCTCTTAATAGCGAAGGTACGTTAGTTACCGATG 5962 aha111, IleMetAspThrLeuProGlyLeuValMetAlaGlnAspGlnArgIleArgTrpTyrLeu
       6001   ATAATGGATACACTACCTGGCTTAGTAATGGCTCAGGATCAAAGGATTCGATGGTATCTG
              TATTACCTATGTGATGGACCGAATCATTACCGAGTCCTAGTTTCCTAAGCTACCATAGAC LeuSerMetGlySerAsnGluAsnIleHisSerIleHisPheSerGlyHisValPheThr
       6061   CTCAGCATGGGCAGCAATGAAAACATCCATTCTATTCATTTCAGTGGACATGTGTTCACT
              GAGTCGTACCCGTCGTTACTTTTGTAGGTAAGATAAGTAAAGTCACCTGTACACAAGTGA ValArgLysLysGluGluTyrLysMetAlaLeuTyrAsnLeuTyrProGlyValPheGlu
       6121   GTACGAAAAAAGAGGAGTATAAAATGGCACTGTACAATCTCTATCCAGGTGTTTTTGAG
              CATGCTTTTTTCTCCTCATATTTTACCGTGACATGTTAGAGATAGGTCCACAAAAACTC ThrValGluMetLeuProSerLysAlaGlyIleTrpArgValGluCysLeuIleGlyGlu
       6181   ACAGTGGAAATGTTACCATCCAAAGCTGGAATTTGGCGGGTGGAATGCCTTATTGGCGAG
              TGTCACCTTTACAATGGTAGGTTTCGACCTTAAACCGCCCACCTTACGGAATAACCGCTC 6223 bsm1,  6227 bgl1, HisLeuHisAlaGlyMetSerThrLeuPheLeuValTyrSerAsnLysCysGlnThrPro
       6241   CATCTACATGCTGGGATGAGCACACTTTTTCTGGTGTACAGCAATAAGTGTCAGACTCCC
              GTAGATGTACGACCCTACTCGTGTGAAAAAGACCACATGTCGTTATTCACAGTCTGAGGG LeuGlyMetAlaSerGlyHisIleArgAspPheGlnIleThrAlaSerGlyGlnTyrGly
       6301   CTGGGAATGGCTTCTGGACACATTAGAGATTTTCAGATTACAGCTTCAGGACAATATGGA
              GACCCTTACCGAAGACCTGTGTAATCTCTAAAAGTCTAATGTCGAAGTCCTGTTATACCT 6305 xmn1, GlnTrpAlaProLysLeuAlaArgLeuHisTyrSerGlySerIleAsnAlaTrpSerThr
       6361   CAGTGGGCCCCAAAGCTGGCCAGACTTCATTATTCCGGATCAATCAATGCCTGGAGCACC
              GTCACCCGGGGTTTCGACCGGTCTGAAGTAATAAGGCCTAGTTAGTTACGGACCTCGTGG 6365 apa1,  6377 bal1, LysGluProPheSerTrpIleLysValAspLeuLeuAlaProMetIleIleHisGlyIle
       6421   AAGGAGCCCTTTTCTTGGATCAAGGTGGATCTGTTGGCACCAATGATTATTCACGGCATC
              TTCCTCGGGAAAAGAACCTAGTTCCACCTAGACAACCGTGGTTACTAATAAGTGCCGTAG LysThrGlnGlyAlaArgGlnLysPheSerSerLeuTyrIleSerGlnPheIleIleMet
       6481   AAGACCCAGGGTGCCCGTCAGAAGTTCTCCAGCCTCTACATCTCTCAGTTTATCATCATG
              TTCTGGGTCCCACGGGCAGTCTTCAAGAGGTCGGAGATGTAGAGAGTCAAATAGTAGTAC
```

FIG. 1J

```
      TyrSerLeuAspGlyLysLysTrpGlnThrTyrArgGlyAsnSerThrGlyThrLeuMet
6541  TATAGTCTTGATGGAAGAAGTGGCAGACTTATCGAGGAAATTCCACTGGAACCTTAATG
      ATATCAGAACTACCCTTCTTCACCGTCTGAATAGCTCCTTTAAGGTGACCTTGGAATTAC

ValPhePheGlyAsnValAspSerSerGlyIleLysHisAsnIlePheAsnProProIle
6601  GTCTTCTTTGGCAATGTGGATTCATCTGGGATAAAACACAATATTTTTAACCCTCCAATT
      CAGAAGAAACCGTTACACCTAAGTAGACCCTATTTTGTGTTATAAAAATTGGGAGGTTAA 6640 sspi, IleAlaArgTyrIleArgLeuHisProThrHisTyrSerIleArgSerThrLeuArgMet
6661  ATTGCTCGATACATCCGTTTGCACCCAACTCATTATAGCATTCGCAGCACTCTTCGCATG
      TAACGAGCTATGTAGGCAAACGTGGGTTGAGTAATATCGTAAGCGTCGTGAGAAGCGTAC GluLeuMetGlyCysAspLeuAsnSerCysSerMetProLeuGlyMetGluSerLysAla
6721  GAGTTGATGGGCTGTGATTTAAATAGTTGCAGCATGCCATTGGGAATGGAGAGTAAAGCA
      CTCAACTACCCGACACTAAATTTATCAACGTCGTACGGTAACCCTTACCTCTCATTTCGT 6738 aha111, 6752 sphi, IleSerAspAlaGlnIleThrAlaSerSerTyrPheThrAsnMetPheAlaThrTrpSer
6781  ATATCAGATGCACAGATTACTGCTTCATCCTACTTTACCAATATGTTTGCCACCTGGTCT
      TATAGTCTACGTGTCTAATGACGAAGTAGGATGAAATGGTTATACAAACGGTGGACCAGA ProSerLysAlaArgLeuHisLeuGlnGlyArgSerAsnAlaTrpArgProGlnValAsn
6841  CCTTCAAAAGCTCGACTTCACCTCCAAGGGAGGAGTAATGCCTGGAGACCTCAGGTGAAT
      GGAAGTTTTCGAGCTGAAGTGGAGGTTCCCTCCTCATTACGGACCTCTGGAGTCCACTTA 6889 mstII, AsnProLysGluTrpLeuGlnValAspPheGlnLysThrMetLysValThrGlyValThr
6901  AATCCAAAAGAGTGGCTGCAAGTGGACTTCCAGAAGACAATGAAAGTCACAGGAGTAACT
      TTAGGTTTTCTCACCGACGTTCACCTGAAGGTCTTCTGTTACTTTCAGTGTCCTCATTGA 6904 bstXI, ThrGlnGlyValLysSerLeuLeuThrSerMetTyrValLysGluPheLeuIleSerSer
6961  ACTCAGGGAGTAAAATCTCTGCTTACCAGCATGTATGTGAAGGAGTTCCTCATCTCCAGC
      TGAGTCCCTCATTTTAGAGACGAATGGTCGTACATACACTTCCTCAAGGAGTAGAGGTCG 6999 xmnI, SerGlnAspGlyHisGlnTrpThrLeuPhePheGlnAsnGlyLysValLysValPheGln
7021  AGTCAAGATGGCCATCAGTGGACTCTCTTTTTTCAGAATGGCAAAGTAAAGGTTTTTCAG
      TCAGTTCTACCGGTAGTCACCTGAGAGAAAAAAGTCTTACCGTTTCATTTCCAAAAAGTC 7029 balI, GlyAsnGlnAspSerPheThrProValValAsnSerLeuAspProProLeuLeuThrArg
7081  GGAAATCAAGACTCCTTCACACCTGTGGTGAACTCTCTAGACCACCGTTACTGACTCGC
      CCTTTAGTTCTGAGGAAGTGTGGACACCACTTGAGAGATCTGGGTGGCAATGACTGAGCG 7116 xbaI, TyrLeuArgIleHisProGlnSerTrpValHisGlnIleAlaLeuArgMetGluValLeu
7141  TACCTTCGAATTCACCCCCAGAGTTGGGTGCACCAGATTGCCCTGAGGATGGAGGTTCTG
      ATGGAAGCTTAAGTGGGGGTCTCAACCCACGTGGTCTAACGGGACTCCTACCTCCAAGAC 7148 ecorI, 7182 mstII,
```

FIG. 1K

```
                GlyCysGluAlaGlnAspLeuTyrOP
      7201      GGCTGCGAGGCACAGGACCTCTACTGAGGGTGGCCACTGCAGCACCTGCCACTGCCGTCA
                CCGACGCTCCGTGTCCTGGAGATGACTCCCACCGGTGACGTCGTGGACGGTGACGGCAGT 7231 ball, 7237 pst1, 7261      CCTCTCCCTCCTCAGCTCCAGGGCAGTGTCCCTCCCTGGCTTGCCTTCTACCTTTGTGCT
                GGAGAGGGAGGAGTCGAGGTCCCGTCACAGGGAGGGACCGAACGGAAGATGGAAACACGA 7321      AAATCCTAGCAGACACTGCCTTGAAGCCTCCTGAATTAACTATCATCAGTCCTGCATTTC
                TTTAGGATCGTCTGTGACGGAACTTCGGAGGACTTAATTGATAGTAGTCAGGACGTAAAG 7381      TTTGGTGGGGGGCCAGGAGGGTGCATCCAATTTAACTTAACTCTTACCTATTTTCTGCAG
                AAACCACCCCCCGGTCCTCCCACGTAGGTTAAATTGAATTGAGAATGGATAAAAGACGTC 7435 pst1, 7438 pvu11, 7441      CTGCTCCCAGATTACTCCTTCCTTCCAATATAACTAGGCAAAAAGAAGTGAGGAGAAACC
                GACGAGGGTCTAATGAGGAAGGAAGGTTATATTGATCCGTTTTTCTTCACTCCTCTTTGG 7501      TGCATGAAAGCATTCTTCCCTGAAAAGTTAGGCCTCTCAGAGTCACCACTTCCTCTGTTG
                ACGTACTTTCGTAAGAAGGGACTTTTCAATCCGGAGAGTCTCAGTGGTGAAGGAGACAAC 7506 xmn1, 7530 stu1, 7561      TAGAAAAACTATGTGATGAAACTTTGAAAAAGATATTTATGATGTTAACATTTCAGGTTA
                ATCTTTTTGATACACTACTTTGAAACTTTTTCTATAAATACTACAATTGTAAAGTCCAAT 7604 hpa1, 7621      AGCCTCATACGTTTAAAATAAAACTCTCAGTTGTTTATTATCCTGATCAAGCATGGAACA
                TCGGAGTATGCAAATTTTATTTTGAGAGTCAACAAATAATAGGACTAGTTCGTACCTTGT 7632 aha111, 7664 bcl1, 7681      AAGCATGTTTCAGGATCAGATCAATACAATCTTGGAGTCAAAAGGCAAATCATTTGGACA
                TTCGTACAAAGTCCTAGTCTAGTTATGTTAGAACCTCAGTTTTCCGTTTAGTAAACCTGT 7741      ATCTGCAAAATGGAGAGAATACAATAACTACTACAGTAAAGTCTGTTTCTGCTTCCTTAC
                TAGACGTTTTACCTCTCTTATGTTATTGATGATGTCATTTCAGACAAAGACGAAGGAATG 7801      ACATAGATATAATTATGTTATTTAGTCATTATGAGGGGCACATTCTTATCTCCAAAACTA
                TGTATCTATATTAATACAATAAATCAGTAATACTCCCCGTGTAAGAATAGAGGTTTTGAT 7861      GCATTCTTAAACTGAGAATTATAGATGGGGTTCAAGAATCCCTAAGTCCCCTGAAATTAT
                CGTAAGAATTTGACTCTTAATATCTACCCCAAGTTCTTAGGGATTCAGGGGACTTTAATA 7921      ATAAGGCATTCTGTATAAATGCAAATGTGCATTTTTCTGACGAGTGTCCATAGATATAAA
                TATTCCGTAAGACATATTTACGTTTACACGTAAAAAGACTGCTCACAGGTATCTATATTT 7981      GCCATTTGGTCTTAATTCTGACCAATAAAAAAATAAGTCAGGAGGATGCAATTGTTGAAA
                CGGTAAACCAGAATTAAGACTGGTTATTTTTTATTCAGTCCTCCTACGTTAACAACTTT 8039 hind111, 8041      GCTTTGAAATAAAATAACAATGTCTTCTTGAAATTTGTGATGGCCAAGAAAGAAAATGAT
                CGAAACTTTATTTTATTGTTACAGAAGAACTTTAAACACTACCGGTTCTTTCTTTTACTA 8081 ball,
```

FIG. 1L

```
8101  GATGACATTAGGCTTCTAAAGGACATACATTTAATATTTCTGTGGAAATATGAGGAAAAT
      CTACTGTAATCCGAAGATTTCCTGTATGTAAATTATAAAGACACCTTTATACTCCTTTTA
```
8133 sspI,

```
8161  CCATGGTTATCTGAGATAGGAGATACAAACTTTGTAATTCTAATAATGCACTCAGTTTAC
      GGTACCAATAGACTCTATCCTCTATGTTTGAAACATTAAGATTATTACGTGAGTCAAATG
```
8161 ncoI,

```
8221  TCTCTCCCTCTACTAATTTCCTGCTGAAAATAACACAACAAAAATGTAACAGGGGAAATT
      AGAGAGGGAGATGATTAAAGGACGACTTTTATTGTGTTGTTTTTACATTGTCCCCTTTAA

8281  ATATACCGTGACTGAAAACTAGAGTCCTACTTACATAGTTGAAATATCAAGGAGGTCAGA
      TATATGGCACTGACTTTTGATCTCAGGATGAATGTATCAACTTTATAGTTCCTCCAGTCT

8341  AGAAAATTGGACTGGTGAAAACAGAAAAAACACTCCAGTCTGCCATATCACCACACAATA
      TCTTTTAACCTGACCACTTTTGTCTTTTTTGTGAGGTCAGACGGTATAGTGGTGTGTTAT

8401  GGATCCCCCTTCTTGCCCTCCACCCCCATAAGATTGTGAAGGGTTTACTGCTCCTTCCAT
      CCTAGGGGGAAGAACGGGAGGTGGGGGTATTCTAACACTTCCCAAATGACGAGGAAGGTA
```
8401 bamh1,

```
8461  CTGCCTGACCCCTTCACTATGACTACACAGAATCTCCTGATAGTAAAGGGGGCTGGAGGC
      GACGGACTGGGGAAGTGATACTGATGTGTCTTAGAGGACTATCATTTCCCCCGACCTCCG

8521  AAGGATAAGTTATAGAGCAGTTGGAGGAAGCATCCAAAGATTGTnACCCAGGGCAAATGG
      TTCCTATTCAATATCTCGTCAACCTCCTTCGTAGGTTTCTAACGTTGGGTCCCGTTTACC

8581  AAAACAGGAGATCCTAATATGAAAGAAAAATGGATCCCAATCTGAGAAAAGGCAAAAGAA
      TTTTGTCCTCTAGGATTATACTTTCTTTTTACCTAGGGTTAGACTCTTTTCCGTTTTCTT
```
8612 bamh1,

```
8641  TGGCTACTTTTTTCTATGCTGGAGTATTTTCTAATAATCCTGCTTGACCCTTATCTGACC
      ACCGATGAAAAAGATACGACCTCATAAAAGATTATTAGGACGAACTGGGAATAGACTGG

8701  TCTTTGGAAACTATAACATAGCTGTCACAGTATAGTCACAATCCACAAATGATGCAGGTG
      AGAAACCTTTGATATTGTATCGACAGTGTCATATCAGTGTTAGGTGTTTACTACGTCCAC
```
8722 tthIII1,

```
8761  CAAATGGTTTATAGCCCTGTGAAGTTCTTAAAGTTTAGAGGCTAACTTACAGAAATGAAT
      GTTTACCAAATATCGGGACACTTCAAGAATTTCAAATCTCCGATTGAATGTCTTTACTTA

8821  AAGTTGTTTTGTTTTATAGCCCGGTAGAGGAGTTAACCCCAAAGGTGATATGGTTTTATT
      TTCAACAAAACAAAATATCGGGCCATCTCCTCAATTGGGGTTTCCACTATACCAAAATAA
```
8852 hpaI,

```
8881  TCCTGTTATGTTTAACTTGATAATCTTATTTTGGCATTCTTTTCCCATTGACTATATACA
      AGGACAATACAAATTGAACTATTAGAATAAAACCGTAAGAAAAGGGTAACTGATATATGT

8941  TCTCTATTTCTCAAATGTTCATGGAACTAGCTCTTTTATTTTCCTGCTGGTTTCTTCAGT
      AGAGATAAAGAGTTTACAAGTACCTTGATCGAGAAAATAAAAGGACGACCAAAGAAGTCA

9001  AATGAGTTAAATAAAACATTGACACATACAAAAAAAAAAAAAAAAAAAAAAAAAAAAAAA
      TTACTCAATTTATTTTGTAACTGTGTATGTTTTTTTTTTTTTTTTTTTTTTTTTTTTTTT

FACTOR VIII:C NUCLEIC ACID MOLECULES

This application is a continuation, of application Ser. No. 07/180,849, filed Apr. 12, 1988 now abandoned, which is a continuation of application Ser. No. 06/757,095, filed 19 Jul. 1985, now abandoned, which is a continuation-in-part of application Ser. No. 06/689,274, filed 7 Jan. 1985 (now U.S. Pat. No. 4,716,117), and a continuation-in-part of application Ser. No. 06/664,919, filed 26 Oct. 1984 (abandoned), which are continuation-in-part applications of application Ser. No. 06/570,062, filed 12 Jan. 1984 now U.S. Pat. No. 5,004,804, the disclosures of which are incorporated herein by reference.

BACKGROUND OF THE INVENTION

1. Field of the Invention

Factor VIIIC is a plasma protein that participates in the intrinsic pathway of blood coagulation. It is absent or defective in individuals with the hereditary X chromosome-linked recessive bleeding disorder hemophilia A. Great difficulty has been encountered in isolating Factor VIIIC due to its extremely low concentration in plasma and the fact that it appears to be an intermediate or final degradation product of a larger protein precursor. Therefore, efforts to isolate Factor VIIIC have led to complex mixtures of significant heterogeneity and varying molecular weights.

One of the approaches which has found broad application to the production of physiologically active proteins involves the isolation of the protein of interest in purified form. The protein of interest provides invaluable aid in the development of a recombinant DNA capability for the production of the protein. By having the protein of interest, one may prepare monoclonal antibodies which are specific for the protein and can be used to establish the production of the protein in lysates, expression from messenger RNA in oocytes, or from a cDNA gene in unicellular microorganisms. In addition, by amino acid sequencing, one can develop probes, employing codons coding for the particular amino acid sequence, for hybridization to messenger RNA, chromosomal DNA or cDNA and, therefore, provide for the detection, isolation and expression of the relevant gene or message and the production of the desired product in high yield in one or more hosts.

2. Description of Relevant Literature

U.S. Pat. No. 4,361,509 and references cited therein describe purification of Factor VIIIC. See also Fulcher and Zimmerman, *Proc. Natl. Acad. Sci. USA* (1982) 79:1648–1652. Tuddenham et al., *J. of Lab. Clinical Medicine* (1979) 93:40–53 describes purification of Factor VIIIC using polyclonal antibodies. Austen, *British J. Hematology* (1979) 43:669–674 describes the use of aminohexyl-Sepharose for Factor VIIIC purification. Weinstein et al., *Proc. Natl. Acad. Sci. USA* (1981) 78:5137–5141 describes a study of the effect of thrombin on Factor VIIIC. See also Kuo et al., Abstracts for IX International Congress of Thrombosis and Hemostasis, (Copenhagen; July, 1983).

SUMMARY OF THE INVENTION

Methods and compositions are provided for the preparation of human Factor VIIIC, precursors and subunits thereof, by production in an expression system, such as a microorganism or mammalian tissue culture. The method-involves isolating pure Factor VIIIC, subunits and fragments thereof and determining their physiological relationship, particularly employing thrombin digestion. At least a portion of each of the related series of polypeptides is sequenced and the sequences employed for developing complex probes. Genomic DNA fragments are probed for homologous sequences and hybridizing fragments isolated and further manipulated to provide a DNA fragment encoding a complete subunit or fragment, essentially free from structural genes present in the normal human chromosome. This fragment may be used for isolating mature mRNA, from which cDNA may be obtained. The DNA sequence may then be further manipulated for insertion into an expression vector and the expression vector employed for introduction into a compatible host for expression of the polypeptide.

BRIEF DESCRIPTION OF THE FIGURES

FIG. 1 provides the nucleotide sequence and putative corresponding amino acid sequence of a full-length cDNA clone exhibiting human Factor VIIIC activity.

DESCRIPTION OF THE SPECIFIC EMBODIMENTS

Figure 2:
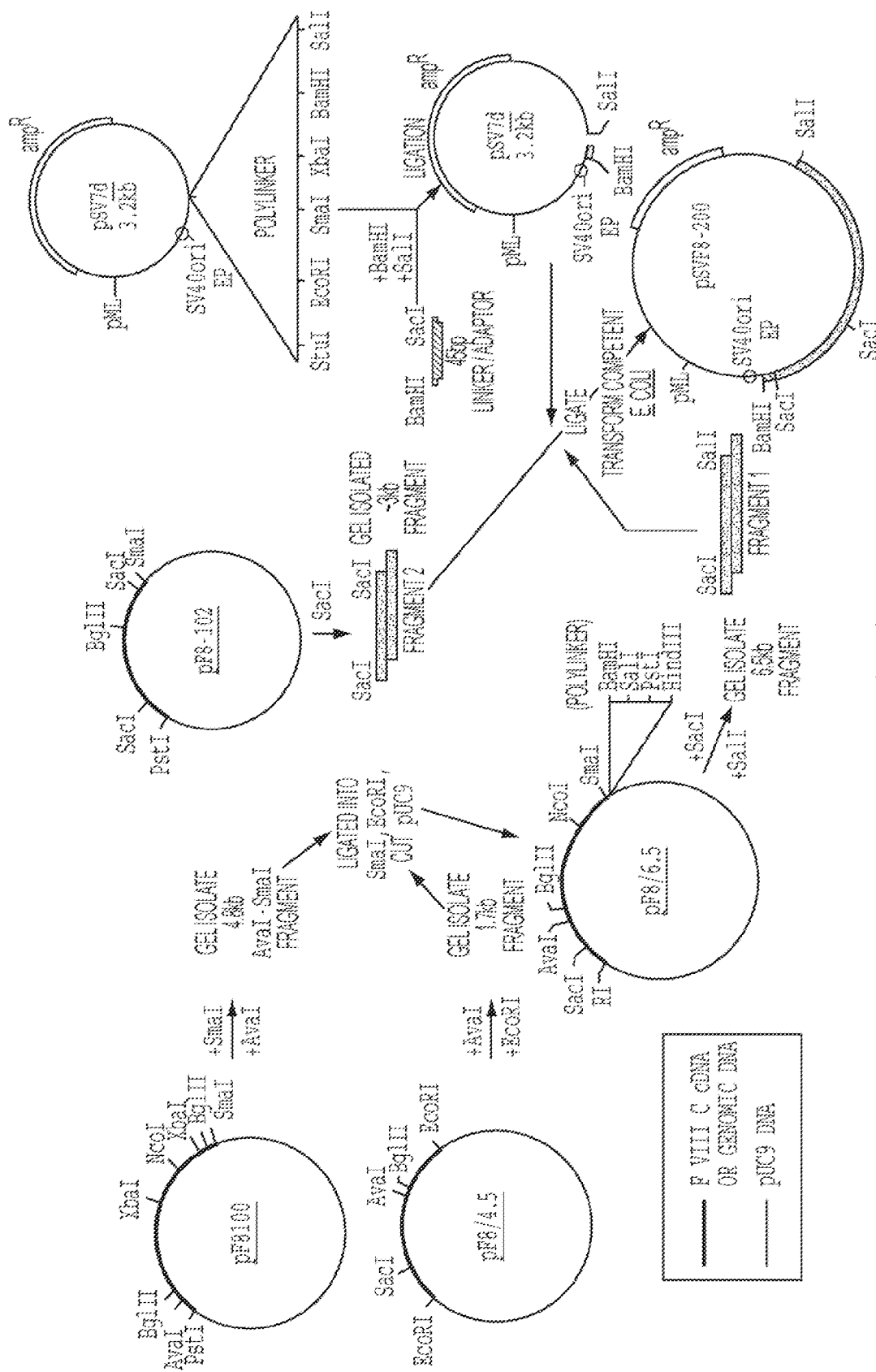
FIG. 2 illustrates the construction of the full-length cDNA encoding human Factor VIIIC in a mammalian expression vector.

Human Factor VIIIC fragments and subunits are provided in substantially pure form. In addition, methods and compositions are provided for the expression of Factor VIIIC subunits and fragments for producing Factor VIIIC as a precursor or in its active form or providing individual subunits for use in combination with naturally available subunits. The subunits and fragments have one or more biological properties associated with Factor VIIIC, such as epitopic sites, coagulation activity, and immunogenicity, so as to be used for producing anti-bodies which find use as reagents, particularly labeled reagents in immunoassays.

Human Factor VIIIC is a complex protein which can be isolated in substantially pure form exhibiting an apparent molecular weight of about 460 kd on SDS polyacrylamide gel electrophoresis. Upon electrophoresis under denaturing conditions, a large number of fragments result of varying molecular weights: 240, 160, 140, 115, 92.5, 80 and 77 kd, the latter two being found to migrate as a doublet. Analysis of the fragments by chemical and protease cleavage (including thrombin) and by employing anti-bodies to follow immunogenic relationships and cleavage patterns to follow structural relationships, demonstrates that the 92.5 kd polypeptide is related to the 240, 160, 140 and 115 polypeptides and from the N-terminal region of the non-reduced protein, while the 77/80 doublet is from the C-Terminal end of the protein. It is further found that the 77/80 kd doublet is converted by thrombin to a 67/70 kd doublet, while the 92.5 kd polypeptide is cleaved by thrombin, directly or indirectly, into two polypeptides of about 40 and 52.5 kd (which can be further cleaved as well). It is found that the electrophoretically isolated 77/80 kd doublet polypeptides have their N-termini blocked, while the 67/70 kd doublet polypeptides do not.

It is further found that the locus for Factor VIIIC involves exons with large introns, where exons involve various domains associated with Factor VIIIC. Thus, individual exons can be isolated which make up specific subunits, or portions thereof, of the Factor VIIIC complex. By identifying specific amino acid sequences involved with Factor VIIIC subunits and portions thereof, one can selectively isolate the exons from genomic DNA and use the exons by themselves, in combination, or joined by synthetic DNA pieces to provide for sequences encoding for polypeptide subunits of Factor VIIIC or fragments thereof.

Conveniently, the Factor VIIIC genomic DNA sequences containing both exons and introns may be inserted into an expression vector appropriate for transcription and translation in mammalian cells to provide for both substantial quantities of messenger RNA suitable for cDNA cloning and production of Factor VIIIC subunits or fragments. In addition, the DNA sequences isolated from the genome can be used for hybridizing to natural messenger RNA (mRNA) encoding for Factor VIIIC. The mRNA may then be used to prepare cDNA encoding Factor VIIIC. The cDNA sequences commonly less than about 10 kb, preferably less than about 7 kb, may be employed for expression by insertion into an appropriate expression vector having the necessary regulatory signals for transcription and translation. The Factor VIIIC gene expression vector (an expression vector carrying one or more genes encoding for all or a portion of Factor VIIIC, precursor, subunits or fragments thereof) may be introduced into a compatible host and the host grown for expression of Factor VIIIC. By appropriate choice of hosts, the Factor VIIIC DNA may be inserted downstream from secretory leader and processing signals, so that the product will be secreted from the host and processed to provide for the complete polypeptide. As appropriate, the polypeptide may be further processed to introduce functionalities or substituents present on the naturally occurring polypeptide.

In the first stage of the subject invention, highly purified Factor VIIIC is obtained and characterized. Purified Factor VIIIC can be obtained from commercially available human anti-hemophilic factor (AHF), which is prepared from fresh, normal human plasma as a cryoprecipitate and represents about a 40-fold enrichment. The Factor VIIIC is further concentrated and purified by dissolving the anti-hemophilic factor into an appropriate buffer, e.g., saline imidazole-lysine-HCl, pH 7.4, followed by chromatography on an affinity column having either polyclonal or monoclonal antibodies to Factor VIIIC or Factor VIIIR. Conveniently, the antibodies are covalently bonded to a Sepharose support. Factor VIIIC may be eluted from the column employing a combination of a relatively high concentration of calcium ion in combination with glycerol. The fractions obtained from the column may then be dialysed with an appropriate buffer, as described above, containing a low concentration of calcium ion and may then be further purified employing an aminohexyl-Sepharose column eluted with a high calcium or sodium chloride concentration buffer. Additional chromatographic steps, e.g., gelatin Sepharose, HPLC, ion exchange on dextran sulfate or Mono Q, affinity columns using lectins or antibodies to Factor VIIIC, provide additional purification. Particularly, the use of dextran sulfate removes trace contamination, e.g., fibrinogen, fibronectin, IgG, from the preparation, so as to leave a product substantially free of foreign proteins. Activity of the fractions from the columns may be monitored for either or both biological and antigenic activity using coagulation assay (commercially available kits) and antibodies specific for Factor VIIIC. Based on the concentration of Factor VIII in plasma, purifications of about 200,000-fold may be achieved by the above-described method.

Characterization of Factor VIIIC

Gel filtration indicates that Factor VIIIC behaves as a complex with an apparent molecular weight of about 460 kd. Using SDS-gel electrophoresis (denaturing conditions) seven individual polypeptides can be isolated of differing molecular weight. The fragments as defined by their molecular weight are 240, 160, 140, 115, 92.5, 80 and 77 kd. These fragments were characterized in the following ways.

The first study involved employing inhibitor antibodies isolated from hemophilic patients, the antibodies being designated as Z and E. Both anti-bodies reacted with the 77/80 kd doublet. The E anti-body reacted strongly with the 240 kd polypeptide and weakly with several bands between the doublet and the 240 kd polypeptide. The Z antibody also reacted weakly with the 240 kd polypeptide.

In immunoprecipitation experiments, the E antibody precipitates the 77/80 kd doublet as well as the high molecular weight species of 160, 140, 115 and 92.5 kd, with the doublet among the stronger bands. Inclusion of EGTA results in the loss of the bands other than the doublet indicating that the 92.5 kd species is associated with the 77 kd and/or 80 kd species in a complex mediated by a $Ca^{++}$ bridge.

In the next study, monoclonal antibodies were prepared, which both inhibit Factor VIIIC mediated coagulation activity and react with components of the complex: Class I reacting with the 77/80 kd doublet and 240 kd polypeptides; Class III reacting with the 160, 140, 115 and 92.5 kd polypeptides. Immunoprecipitation of thrombin-digested Factor VIIIC with Class I antibodies indicates that the resulting 70/67 kd doublet is derived from the 77/80 kd doublet present in Factor VIIIC. The Class III monoclonals indicated that the 160, 140 and 115 kd peptides are precursors of the 92.5 kd peptide. A 40 kd peptide cleavage product of 92.5 kd peptide was also bound by the Class III antibodies. An ELISA assay using monoclonal antibodies in the presence and absence of EGTA confirms the $Ca^{++}$ bridge association between the 92.5 kd and 77 kd and/or 80 kd components of the Factor VIIIC complex.

Both the human inhibitor and monoclonal antibodies may be used in immunosorbent column procedures to obtain Factor VIIIC or using EGTA, to resolve its constituent components, the 92.5 kd and 77/80 kd species.

The next study involved thrombin degradation of purified Factor VIIIC material at pH 6.8 or 7.4. Aliquots were assayed for coagulation activity and TCA precipitated for gel analysis. Coagulation activity was shown to increase with time and then decrease coincidently with an increase and decrease in the amount of the 92.5 kd species. Thrombin treatment of the purified Factor VIIIC material for short periods of time (5–15 min) enhances the amount of 92.5 kd species, while the 77/80 kd doublet is partially converted to a 67/70 kd doublet. When long thrombin digestion times are employed, e.g., one hour, the 92.5 kd protein is degraded and two new peptides of 40 and 52.5 kd appear, with the 40 kd peptide retaining immunogenic characteristics of the 92.5 kd species. The 52.5 kd peptide is shown to be a cleavage product by chemical and enzymatic degradation patterns and products analogous to the 92.5 kd species.

In the next study individual Factor VIIIC subunits and precursors (e.g., 240, 77/80, 92.5 kd species) were isolated by preparative SDS gel electrophoresis and a time course thrombin digestion of the isolated polypeptides was then performed. The 240 kd fragment isolated from a preparative gel produced 160, 140, 115, and 92.5 kd bands. The 80 kd and 77 kd fragments produced a 70 kd and 67 kd fragment, respectively.

A Factor VIIIC complex is derived containing the 77 kd and/or 80 kd species and 92.5 kd polypeptide as a calcium-bridged complex in highly purified form. The purity of Factor VIIIC material (the complex and precursor species) is usually greater than 80%, often greater than 90%, and may be 98% or higher based on total protein, and that of the complex at least 20%, more usually 30% based on total protein, following the anti-Factor VIIIR immunosorbent and aminohexyl Sepharose columns. The use of additional chromatographic steps, e.g., dextran sulfate, increases the level of purity to at least 90% and usually greater for the Factor VIIIC material (complex plus precursor). The purity of Factor VIIIC components, 92.5 kd species and the 77/80 kd doublet, isolated by preparative SDS gel electrophoresis is usually at least 98%. As indicated above, the complex can be obtained using monoclonal antibodies specific for a member of the doublet, or for the 92.5 kd polypeptide. The complex may then be separated from the antibody using a denaturing or chaiotropic solvent, e.g., aqueous urea or thiocyanate, respectively.

Preparation of Probes

A partial amino acid sequence of the N-terminus of the 67 and 70 kd polypeptides is as follows:

```
    1   2   3   4   5   6   7   8   9   10  11
    ?   Phe Gln Lys Lys Thr Arg His Tyr Phe Ile 12  13  14  15  16  17  18  19  20  21  22
   Ala Ala Val Glu Arg Leu Trp Asp Tyr Gly Met
```

Based on this sequence, probes for the 67/70 kd doublet (and thus the 77/80 kd doublet from which it is derived) may be prepared having the following sequences:

```
Probe 1: 3' GTA ATA AAA TAA CGX CGX CA 5'
(non-coding)   G   G   G   G
                           T Probe 2: 3' AAA GTT TTC TTC TGX TCT GT 5'
(non-coding)   G   C   T   T       C
                                  GCX Probe 3: 5' GAA CGX TTA TGG GAT TAT GGX ATG 3'
(coding)        G AGA   G           C   C
                    G CTX Probe 4:
(non-coding)
3' TCT GTA ATG AAA TAG CGA CGA CAC CTT TCT GAC ACC CTA ATG CCG TAC 5'
    C   G       G       G   G   C   C           G
(X=G,C,A,T)
```

The N-terminus amino acid sequence of the 52.5 kd protein is substantially as follows:

```
 1   2   3   4   5   6   7   8   9   10  11  12  13
Ala Thr Arg Arg Tyr Tyr Leu Gly Ala Val Glu Leu Ser 14  15  16  17  18  19  20  21  22  23  24  25  26
Trp Asp Tyr Met Gln Ser Asp  ?  Gly Glu Leu Pro Val
```

Based on this amino acid sequence, a probe for the 52.5 kd protein may be prepared based on the coding strand as follows:

```
5'- GCA ACT AGA AGA TAT TAT TTG GGG GCA GTT GAA TTG TCA TGG GAT TAT -3'
        A   G   G           A   A       A       A   T
```

The amino acid sequences of three fragments of the 77/80 kd proteins are as follows:

```
 1   2   3   4   5   6   7   8   9   10  11  12
Tyr Ala Ala Thr Ser Gln Val Leu Leu Pro Ser Lys 1   2   3   4   5   6   7   8   9   10
Val Thr Gly Val Thr Thr Gln Gly Val Lys 1   2   3   4   5   6   7   8   9   10  11  12
Met Glu Val Leu Gly Gys Glu Ala Gln Asp Leu Tyr
```

Based on these sequences respectively, probes may be prepared based on the non-coding strands as follows:

```
Probe 1: 3'-ATA CGT CGT TGA AGT GTT CAA AAC AAC GG-5'
                     T   A       T   T   T Probe 2: 3'-CAA TGA CCT CAA TGA TGA GTT CCT CAA TTT-5'
            T   T       T   T   T           T Probe 3: 3'-TAC CTT CAA AAC CCT ACG CTT CGT GTT CTA AAC ATA-5'
                T   T                               T
```

Sequences of these peptides and preparation of the corresponding probes are described in detail in the Experimental section hereinafter.

Isolation of DNA

The above probes can be used for the detection and isolation of either genomic DNA or messenger RNA. Cloning genomic DNA involves cleavage of the genomic DNA with one or more restriction enzymes to obtain a partial digest and size selection of fragments of about 10–25 kb. The restriction digests should be incomplete so that there will be overlapping fragments cloned. These fragments may be cloned in the appropriate vector to produce a "library" of clones in microorganisms, e.g., bacteria, such as E. coli. Various vectors may be employed, including plasmids or viruses, such as pBR322, lambda, charon 4A, EMBL-4, or the like.

The DNA is screened with the enzymatically radiolabeled probes described above and homologous sequences detected. Those sequences which hybridize with one or more of the probes may be recloned and again rehybridized one or more times.

One or more restriction enzymes different from the original restriction enzyme(s) employed may then be used to provide for smaller fragments, generally ranging from about 1–10 kb, more usually from about 1–6 kb. These fragments may then be subcloned and screened to identify positive fragments. The synthetic probes can then be used as primers for sequencing of the DNA fragments. Fragments which may be most conveniently sequenced are those which include a sequence complementary to one or more of the above-identified probes, where the homologous sequence is from about 5 bases and up to not more than about 500 bases from the 5'-terminus. Other fragments of interest include those at the termini of the original cloned fragment since these will be represented in other clones in the library and thus used to "walk" along the chromosome until the entire desired gene is recovered.

After sequencing the DNA fragment, based on the determined sequence, the fragment will be further manipulated. Based on the sequence, one can identify an open reading frame including the determined amino acid sequence. By determining restriction sites, one can further reduce the size of the fragment, without loss of coding sequences, although removal of a short sequence at the N-terminus is permissible, since this can be replaced by using appropriate adapters. Where restriction sites are not readily available at appropriate positions, the DNA fragment may be modified by Bal31 resection for varying times, the resulting fragments cloned, and the 5'-termini determined by various techniques. Conveniently, one can provide for a recognition site of a particular restriction enzyme by appropriate selection of the 3'-bases to which the resected fragment is joined. In this way, one can screen the resulting clones for the predetermined restriction site, which will indicate the presence of a fragment resected to the desired site.

Desirably exons or fragments thereof, usually of at least 50 bp, more usually of at least about 100 bp, even about 250 bp or more, may be denatured and used as probes for mRNA from human cells, particularly cells producing mRNA for Factor VIIIC. By isolating hybridizing mRNA, the mRNA may be screened by translation in oocytes or a reticulocyte lysate and production of Factor VIIIC detected by antibodies to Factor VIIIC or coagulation activity based on binding to Factor VIIIC subunits. The mRNA may then be reverse transcribed, using, for example, AMV reverse transcriptase. Various methods can be used for converting ss cDNA to ds cDNA, using the reverse transcriptase or DNA polymerase I (Klenow fragment) to produce the second strand, followed by removal of the terminal loop, as appropriate, with a nuclease, e.g., $S_1$ nuclease. Where an incomplete copy is obtained, the messenger may be "walked" or primed cDNA synthesis may be used until the 5'-coding sequence of the mRNA has been copied and a DNA sequence encoding for the entire coding region of the mRNA is obtained.

Based on the above procedures, DNA sequences coding for the polypeptide precursor(s) to Factor VIIIC or major fragments thereof may be used for expression, or smaller fragments coding for specific subunits of Factor VIIIC, e.g., 92.5 kd, 80 kd or 77 kd, may be employed.

For the precursor polypeptide, (proFactor VIIIC), the gene may be blunt-ended at one or both ends and inserted into an expression vector having complementary ends, or may be cleaved downstream from the 5'-coding terminus and joined to an adapter for appropriate insertion into the vector.

Fragments having the proper N-terminus, which may be at the coding sequence for the 70 kd or 80 kd polypeptide or may have a 5'-terminus downstream from the initial base, usually not more than about 30 bases downstream, more usually not more than about 20 bases downstream, may then be inserted into an appropriate vector using adapters, as appropriate.

Various vectors may be employed for providing extrachromosomal elements, depending upon the particular host, the manner of expression, whether constitutive or induced, the desired markers, whether secretion is desired, or the like. (By vector is intended an intact replication system.) Numerous vectors are presently available which provide for the transcriptional and translational regulatory signals recognized either by mammalian hosts, e.g., tissue culture cells or by prokaryotic and eukaryotic microorganism hosts, e.g., E. coli, B. subtilis, B. thermophilus, S. cerevisiae, or the like.

The vectors will have a replication system recognized by the host, although in some instances, integration of a construct having transcriptional and translational regulatory signals and the cistron of interest into the host genome may be desirable. In those situations, the construct will usually be flanked by sequences homologous to sequences in the host genome.

The expression vectors which are employed will have transcriptional and translational signals recognized by the host. The transcriptional signals will include the promoter and terminator, as well as auxiliary signals such as one or more enhancers. In addition, regulation of transcription may be provided, by including operators, activators, genes providing for repression, or the like. Other sequences involved with transcription include capping, polyadenylation, etc. For translation, depending upon the host, there may be a ribosomal binding site, an initiation codon, stop codons, or the like.

Conveniently, non-coding 5'- and 3'-flanking regions will be employed from genes native to the host, so that the signals recognized by the host will be present in appropriate relationship. These flanking regions can be joined to the gene encoding for the Factor VIIIC precursor, subunit or fragment thereof, so that the gene is in reading frame with the initiation codon and either carries its own stop codon or is inserted immediately upstream from one or more stop codons.

A vector will normally have one or more markers which provide for selection and allow for continued selective pressure during growth of the host. These markers may include prototrophy in an auxotrophic host, antibiotic resistance, toxin resistance, etc.

Where a secretory leader and processing signals are provided, it will usually be necessary to provide an adapter. By providing for an appropriate restriction site at the terminus of the DNA sequence encoding secretory leader and processing signals or upstream therefrom, one can synthesize an oligonucleotide adapter, usually of from about 10–50 bp, which can be inserted between the secretory leader and processing signals or truncated portion thereof, and the gene of interest, which has a 5'-terminus at the initial codon of the gene or downstream thereof, so that the adapter restores all of the necessary missing bases and provides for the gene being in reading frame with the initiation codon of the leader sequence.

The resulting constructs which include the desired gene may then be introduced into a host, capable of growth in culture, in accordance with conventional methods, e.g., transformation, conjugation, transfection, or the like. The host may then be grown in an appropriate nutrient medium and the product isolated in accordance with conventional ways. Where the product is retained intracellularly, the cells will be harvested and lysed; where secreted, the product will be isolated from the nutrient medium. The product may be purified by chromatography, e.g., affinity chromatography, electrophoresis, extraction, HPLC, or the like.

For expression in a mammalian cell a mammalian virus may be employed as the vector, e.g., SV-40, papilloma virus, Maloney murine sarcoma virus, adenovirus, or the like. These viruses have been modified for use as expression vectors in mammalian cell cultures. An illustrative system employs COS cells bearing an integrated SV-40 genome and producing the large T antigen required for SV-40 replication (Gluzman, Cell (1981) 23:175). A fragment spanning the HpaI site at 0.76 on the SV-40 map to the BamHI site at 0.14 on the SV-40 map may be used as a vector. The recombinant plasmid obtained by joining the Factor VIIIC gene or portion thereof with the SV-40 vector may be used to transfect monkey CV-1 cells.

In accordance with the subject invention, purified subunits and fragments of Factor VIIIC may be obtained and used to enhance clotting capability for individuals requiring the particular subunit. The Factor VIIIC may also be used in therapy. In addition, the polypeptides prepared according to this invention can be used for the production of monoclonal antibodies to Factor VIIIC, its subunits and fragments. Also, the subunits and fragments may be used as reagents, which may be labeled and in combination with the antibodies, employed in diagnostic assays for the presence of one or more subunits or degradation fragments thereof in physiological fluids, e.g., blood or serum.

The following examples are offered by way of illustration and not by way of limitation.

Whenever used hereinafter Ab intends antibody and Ag antigen.

EXPERIMENTAL

I. Purification of Factor VIIIC

Human Factor VIIIC was isolated from commercial cryoprecipitate preparations by a) immunosorbent chromatography using a polyclonal anti VIIIR-Sepharose column by a method first described by E. G. D. Tuddenham, N. C. Trabold, J. A. Collins, and L. W. Hoyer, *J. of Lab. Clinical Medicine* (1979) 93:40; and b) a chromatographic separation on aminohexyl-substituted agarose as was originally described by D. E. G. Austen, *British J. of Hematology* (1979) 43:669.

Details of the procedures are described below.

Goat anti-human Factor VIII Related Antigen (VIII:R) serum obtained from *Atlantic Antibody* (cat. no. 040-01), was treated with either a standard 0–50% ammonium sulfate cut followed by DEAE cellulose column chromatography, or a similar 0–33% cut without subsequent chromatography. These materials were then conjugated to CNBr-activated Sepharose CL2B or 4B, respectively, (Pharmacia, 17-0140-01 or 17-0430-01) and poured as a column anti VIII:R-Sepharose column).

"HEMOFIL", a stable, dried preparation of antihemophilic factor (Factor VIII, AHF, AHG) in concentrated form prepared from fresh, normal human plasma, representing about a 40-fold enrichment for Factor VIIIC, was dissolved in the following buffer: 0.02M imidazole, 0.15M NaCl, 0.1M lysine-HCl, 0.02% $NaN_3$, pH 7.4.

After being dissolved, the Hemofil was applied to the above-described anti VIII:R-Sepharose column. Non-specifically bound protein was eluted with the above buffer modified to 0.5M NaCl. Next, Factor VIIIC was eluted with the above buffer containing 0.35M $CaCl_2$, with the addition of 10% glycerol which stabilizes the Factor VIIIC activity. Active fractions from the immunosorbent column were pooled and dialyzed against buffer (0.02M imidazole, 0.15M NaCl, 0.1M lysine-HCl, 0.025M $CaCl_2$, 0.02% $NaN_3$, 10% glycerol, pH 7.4). An aliquot of the dialyzed fractions, which contained 1,100 units of Factor VIIIC, was applied to an aminohexyl-Sepharose 4B column (1×6 cm) equilibrated with dialysis buffer described above. Factor VIIIC activity was eluted with the same buffer containing either 0.35M $CaCl_2$ or 2M NaCl. The activity was found to be in a volume of 2 ml with 500 units of Factor VIIIC per ml. Subsequent experiments carried out in the same manner provided a recovery of 25% off the anti VIII:R column and a recovery of approximately 90% off the aminohexyl column. Alternatively, pooled, dialysed material eluted from the immunosorbent column is first applied to a dextran sulfate (Pharmacia) column (1.5×6 cm) equilibrated with the dialysis buffer above and eluted with the same buffer. Several minor contaminants, e.g., fibrinogen, fibronectin, IgG, are retained on the column while Factor VIIIC emerges in the flow-through which is collected and loaded on the aminohexyl-Sepharose column as before.

Both biological, i.e., clotting, and antigenic (cAg) activity were shown to be present in the purified Factor VIIIC, as demonstrated by the subsequent assays indicating a 5,000-fold purification over the 40-fold concentration in Hemofil. Using a standard commercially available three component kit from General Diagnostics, Inc. (APTT, Factor VIII deficient plasma, Verify Normal Citrate; Morris Plains, N.J.) a coagulation assay was carried out and indicated high levels of Factor VIIIC biological activity. (See generally, Hardisty, R., et al., "A One Stage Factor VIII Assay and Its Use on Venous and Capillary Plasma," *Thombosis et Diathesis Haemorrhagica* (1962) 7:215–299; and Owen, C., et al., *The*

*Diagnosis of Bleeding Disorders*, 2d ed., Little, Brown & Co., Boston, 1974, both of which are incorporated herein by reference.)

Antibodies employed were derived from inhibitor patients, one with a low titer (LZ) as coating ab and one with a high titer (HZ) as the labeled ab. The antibodies were used in two different types of assays. In an RIA assay, the HZ ab is labeled with $I^{125}$, while in an ELISA assay the HZ ab is coupled to horseradish peroxidase. Labeling with $^{125}I$ of antibody HZ for the RIA was performed in accordance with Hunter, W. M., In Radioimmunoassay, Weir, D. M., ed., Handbook of Experimental Immunology, 3rd ed., vol. 1, Blackwell Scientific Publications, Oxford, 1978. HRP-HZ conjugation was in accordance with Wilson and Nakane, In Immunofluorescence and Related Staining Techniques, Knapp et al., eds., Elsevier, North-Holland Biomedical Press, Amsterdam, 1978, pp. 215–224. LZ had an activity of 700 Bethesda Units/ml while HZ had an activity of 1,500 Bethesda Units/ml. Coating antibody (LZ) was diluted to 3.5 µg/ml in 0.1M $NaHCO_3$, pH 9.8 (RIA) or 0.05M imidazole, 0.1M NaCl, 0.01% Thimerosal, 0.05% Tween 20, 5% BSA (ELISA) or for either method PBS-CMF (for 1 liter: 200 mg KCl, 200 mg $KH_2PO_4$, 8.0 g NaCl, 1.15 g anhydrous $Na_2HPO_4$, pH 7.4) and 1 ml added to each tube (polystyrene) and incubated overnight at room temperature. This solution is removed by suction and the tubes washed 3× with 3–3.5 ml 0.15M NaCl or PBS-CMF containing 0.05% Tween 20. Samples or standards (General Diagnostics, Verify Normal Citrate, catalog #34112) are diluted and added to the tubes to a total volume of 0.9 ml per tube and incubated overnight at room temperature (dilutions were made in 0.02M Tris, 0.15M NaCl, 5% BSA, 0.05% Tween 20, 0.01% Thimerosal, pH 6.5 for RIA or 0.05M imidazole, 0.1M NaCl, 0.01% Thimerosal, 0.05% Tween 20, 5% BSA for ELISA or PBS-CMF for either method). Solutions were removed by suction and tubes washed as before. For RIA, $5 \times 10^5$ cpm of $^{125}I$-labeled antibody to Factor VIIIC (HZ) in 600 µl of RIA dilution buffer was added to each tube which was then incubated at 37° C. for 16–18 h; solutions were removed, the tubes washed as before and counted in a gamma counter. For ELISA, 0.9 ml peroxidase conjugated anti-Factor VIIIC (HZ) was added to each tube which was then incubated overnight at room temperature; solutions were removed and the tubes washed as before, then 0.9 ml OPD solution (for 100 ml: 0.73 g citric acid, 1.19 g disodium acid phosphate, 0.15 g o-phenylenediamine, pH 5.0 with 250 µl 10% $H_2O_2$ added immediately before use) added and incubated at room temperature for 30 min in the dark. To stop this reaction, 0.5 ml of 6N HCl (or 0.9 ml 1M $H_2SO_4$) was added to each tube and the $OD_{492}$ read.

II. Structure of the Factor VIIIC Complex

A. Immunoprecipitation Experiments

Gel filtration experiments were carried out with an AcA 44 column on the Factor VIIIC purified material under the following conditions: 0.1% insulin (as carrier protein for stabilization), 0.25M $CaCl_2$, 0.01% Thimerosal, 0.05M imidazole, pH 7.2. The Factor VIIIC coagulation and antigenic activities of the eluate were monitored. Two antigenic peaks were observed. One with Factor VIIIC coagulation activity behaved as a complex with an apparent molecular weight of about 460,000 under these conditions (native). The other peak (devoid of coagulation activity) eluted at an observed molecular weight slightly below 67,000.

When analyzed by standard analytical Laemmli SDS-gel electrophoresis (Laemmli, *Nature* (1970) 227:680–685), various protein species of 240, 160, 140, 115, 92.5, 80 and 77 kd were obtained. The relationship of these proteins to Factor VIIIC was determined by standard immunoprecipitation procedures. In the immunoprecipitation procedure, *S. aureus* protein A-Sepharose CL4B or polystyrene beads (⅛ in, Precision Plastic Ball Co.) coated with affinity purified second antibody (goat anti-mouse IgG or anti-human IgG) were employed to separate antigen-Ab complexes from free $^{125}I$-labeled Factor VIIIC.

The proteins eluted from the affinity column were iodinated and then reacted with antibodies specific for Factor VIIIC. The antibodies were human inhibitor antibodies isolated from hemophiliac patients and referred to as anti-Factor VIIIC (Z) and (E) or inhibitor antibody (Z) and (E).

The results indicated that both antibodies reacted with the 77/80 kd doublet. The "E" antibody also reacted strongly with the 240 kd band and gave weak precipitation of several bands (160, 140, 115, 92.5 kd) between the doublet and 240 kd species. The "Z" antibody also precipitated the 92.5 kd and 240 kd proteins. The strong reaction of the "E" antibody with the 240 kd species suggests that this species is a precursor of Factor VIIIC.

The antibody-column purified Factor VIIIC fraction was iodinated and reacted with the human inhibitor antibody in the presence and absence of EGTA (ethylene glycol bis(β-aminoethyl ether) N,N,N',N'-tetracetic acid). This allows for an investigation of the role of divalent cations, particularly $Ca^{++}$, in the association of the Factor VIIIC polypeptides. It was observed that the inhibitor antibody (E) precipitates the 77/80 kd doublet, as well as higher molecular weight species of 160, 140, 115 and 92.5 kd. The doublet is always among the stronger bands. (This immunoprecipitation experiment was done with the polystyrene beads. This procedure results in lower backgrounds and the labeled IgG in the Factor VIIIC preparation is not precipitated). Inclusion of EGTA results in the loss of the higher molecular weight bands (92.5–160 kd) but has no effect on the amount of doublet precipitated. A similar experiment utilized Z antibody coupled to Sepharose as an immunosorbent: purified Factor VIIIC is applied to the column and after binding via 77/80 kd, the 92.5 kd polypeptide is selectively eluted with EDTA (ethylene diamine tetraacetic acid). The method is used preparatively to fractionate the 92.5 kd species. This immunosorbent column or a similar one are prepared with polyclonal antibodies to Factor VIIIC. When eluted with chaotropic or denaturing solvents, e.g., thiocyanate solutions or aqueous urea, respectively, rather than EGTA, Factor VIIIC is further purified. These results suggest that the 92.5 kd peptide may be associated noncovalently to the 77/80 kd doublet via a $Ca^{++}$ bridge. Inhibitor antibody appears to interact directly only with the doublet. The higher molecular weight bands (the 115 kd, 140 kd, 160 kd) are probably precursors of 92.5 kd, as indicated by the ability of the monoclonal antibody directed against the 92.5 kd polypeptide to cross-react with the 115 kd, 140 kd and 160 kd polypeptides.

The relationship of various protein species from the affinity column was demonstrated by immunoprecipitation of iodinated, purified Factor VIIIC with monoclonal antibodies prepared according to the method of G. Kohler and C. Milstein (*Eur. J. of Immunol.* (1975) 6:511). Balb/c mice were immunized with liquid phase immunoadsorbed Factor VIIIC. Spleen cells ($10^8$) were fused with $10^7$ NSO or NSI mouse myeloma cells. The fusion products were plated into two 96-well microtiter trays. A spleen cell feeder layer was used at $10^4$ cells/well. Colonies were microscopically visible from the fifth day and the supernatants assayed every few days using an ELISA assay. The following layers were employed: 1st, Factor VIIIC eluted from hexyl-Sepharose 4B column, as described in Section I above; 2nd, hybridoma cell supernatant; 3rd, horseradish peroxidase (HRP)-labeled goat anti-mouse IgG; 4th, HRP-substrate.

Several classes of monoclonal antibodies were identified, two of which inhibited Factor VIIIC coagulation activity: Class I antibodies reacted with the 80/77 kd doublet and 240 kd polypeptides; and Class III antibodies reacted with proteins of 240, 160, 140, 115, 92.5 kd. Immunoprecipitation of thrombin-digested Factor VIII with Class I monoclonal antibodies indicates that the 70/67 kd doublet produced is derived from 77/80 kd doublet (see below). Class III monoclonal antibodies indicate that the 160, 140 and 115 kd peptides are precursors of 92.5 kd peptide. The monoclonal antibodies of Class III further reacted with a 40 kd peptide produced by thrombin digestion of the purified Factor VIIIC material.

An experiment similar to that described above, using EGTA to investigate the role of $Ca^{++}$ ion in the Factor VIIIC complex, was also performed utilizing a monoclonal antibody based ELISA assay with the following layers: 1st, monospecific anti(mouse IgG); 2nd, Class III monoclonal antibody (anti-92.5 kd); 3rd, purified Factor VIIIC material; 4th, HRP-human inhibitor antibody to 77/80 kd. Addition of EGTA removed bound HRP activity present in the control without chelator. The fact that the Class I and III monoclonal antibodies directed to the 77/80 kd doublet and 92.5 kd proteins, respectively, are each inhibitory to Factor VIIIC coagulation activity implicates both as essential components of the Factor VIIIC complex.

B. Thrombin Activation of Factor VIIIC

Aminohexyl-concentrated, affinity-purified Factor VIIIC has been activated by thrombin (Boehringer, lot #1072302) using two different sets of pH conditions (6.8 and 7.4).

Aliquots were assayed for coagulation activity and, in addition, samples (about 2.5 units each) were TCA precipitated for gel analysis. In the first experiments, the VIIIC activity was initially 46 units/ml. This was diluted to a final concentration of 11.5 units/ml in Factor VIIIC buffer (20 mM imidazole, pH 6.8, 150 mM NaCl, 100 mM lysine, 25 mM $CaCl_2$ and 10% glycerol). The final concentration of thrombin was 0.12 unit/ml (about 1 unit of thrombin per 100 coagulation units of VIIIC). The results showed that the coagulation activity increases to about 180 units/ml then decreases to about 40 units/ml (essentially the starting value) coincidentally with a similar increase and decrease in the amount of 92.5 kd species. Thus the 92.5 kd species is implicated as part of the active Factor VIIIC complex.

Additional experiments with more concentrated Factor VIIIC preparations were carried out for the purpose of using thrombin activation in a preparative manner. To generate 92.5 kd polypeptide, thrombin was added to the purified Factor VIIIC material (pH 7.4) at a ratio of about 1000–2000 coagulation units of Factor VIIIC to 1 unit of thrombin activity and allowed to react for only a short period of time (5–15 min, depending on the Hemofil sample). The resulting product was then applied to a 7.5% preparative gel and peptides separated by electrophoresis, the gel bands cut out and electroeluted.

When thrombin digestion is carried out for a short time, the amount of 92.5 kd species can be doubled or tripled; at the same time, the 77/80 kd doublet is only partially converted to 67/70 kd species. To optimize conditions for isolation of the 67/70 kd doublet, a longer time course (greater than 1 h) thrombin digestion is carried out. In this case, the 92.5 kd species is further cleaved to produce smaller fragments. Two new peptides, 52.5 kd and 40 kd appear after thrombin treatment. The 40 kd peptide reacts with the monoclonal antibody directed against the 92.5 kd species and must therefore be a cleavage product. The 52.5 kd peptide is also derived from the 92.5 kd protein as demonstrated by a comparison of chemical and enzymatic cleavage patterns, i.e., both the 92.5 kd and 52.5 kd species when subjected to CNBr or endoproteinase lys C cleavage show a number of common fragments (by SDS-PAGE).

For endoproteinase lys C digestion, a weight ratio of lys C to protein of from about 1:1–100, usually 1:10, is used. In the subject digestion, 20 pmoles (4.8 μg) lys C was combined with 200 pmoles (14 μg) 70 kd polypeptide in about 100 μl 0.025M Tris-HCl, pH 7.7, 0.001M EDTA, 0.08% SDS and the mixture incubated at 37° C. for 6 h to overnight for complete digestion. Native polyacrylamide gels according to Orstein, *Ann. N.Y. Acad. Sci.* (1964) 121:321–349 were used for isolation of lys C digestion products.

C. Thrombin Digestion of Gel Isolated VIIIC-Related Proteins

In order to confirm the precursor-product relationship of these peptides, a number of the bands were isolated by preparative SDS gel electrophoresis, electroeluted and subjected to thrombin digestion. The results were as follows:

1. The 240 kd protein produced multiple bands including 160, 140, 115, 92.5 kd but nothing smaller than 92.5 kd, i.e., no 77/80 kd or 67/70 kd doublet. In addition, a time course for digestion was carried out with the 240 kd fragment and analyzed for gel electrophoresis pattern, coagulation activity, and Factor VIIIC antigenic (Cag) activity. Gel results were the same as above and essentially no Cag or coagulation activity was recovered.

2. The 160 kd and 92.5 kd gel-isolated polypeptides do not appear to be substrates for thrombin after isolation from the gel.

3. Thrombin specifically cleaves gel isolated 77 kd and 80 kd species to produce new polypeptides of 67 kd and 70 kd, respectively. After thrombin treatment, monoclonal antibodies of Class I precipitate not only the 77/80 kd doublet, but also the new 67 and 70 kd species.

D. Amino Acid Sequence Analysis

Partial amino acid sequence information was obtained by standard procedures for the 67/70 kd peptides, the 77/80 kd peptides and the 52.5 kd peptide isolated by preparative SDS electrophoresis. The electrophoretic analysis, together with the amino acid sequence results, indicated that the gel-isolated 77/80 kd, 67/70 kd, 92.5 kd and 52.5 kd polypeptides were obtained at >95%, usually 98%, purity. The gel isolated peptides were applied to a gas phase protein sequencer (Applied Biosystems). The PTH-amino acids were applied to an HPLC column (IBM cyano, 25 cm) and the amino sequence determined from the resulting chromatograms.

The following sequence was determined for the 67/70 kd doublet at its amino terminus (indicated with a bar in Appendix B):

| 1 | 2 | 3 | 4 | 5 | 6 | 7 | 8 | 9 | 10 | 11 |
|---|---|---|---|---|---|---|---|---|----|----|
| ? | Phe | Gln | Lys | Lys | Thr | Arg | His | Tyr | Phe | Ile |

| 12 | 13 | 14 | 15 | 16 | 17 | 18 | 19 | 20 | 21 | 22 |
|----|----|----|----|----|----|----|----|----|----|----|
| Ala | Ala | Val | Glu | Arg | Leu | Trp | Asp | Tyr | Gly | Met |

Using the information provided by the amino acid sequence of the N-terminal region of the 67/70 kd protein the following oligonucleotide probes were synthesized to be used to screen human genomic libraries. The phosphoramidite method as described by M. S. Urdea et al., *Proc. Natl. Acad. Sci. USA* (1983) 80:7461–7465 was used:

```
Probe 1: 3' GTA ATA AAA TAA CGX CGX CA 5'
              G   G   G   G
                          T Probe 2: 3' AAA GTT TTC TTC TGX TCT GT 5'
              G   C   T   T       C
                              GCX Probe 3: 5' GAA CGX TTA TGG GAT TAT GGX ATG 3'
              G AGA  G           C   C
                G CTX Probe 4:
3' TCT
GTA ATG
AAA TAG
CGA CGA
CAC CTT
TCT GAC
ACC CTA
ATG CCG
TAC 5'
              C   G       G       G   G       C   C           G
(X=G,C,A,T)
```

A scheme showing regions of amino acid sequence from which each probe is derived is shown below:

```
 1   2    3    4    5    6    7    8    9   10   11   12   13   14   15   16   17   18   19   20   21   22
 ?  Phe  Gln  Lys  Lys  Thr  Arg  His  Tyr  Phe  ile  Ala  Ala  Val  Glu  Arg  Leu  Trp  Asp  Tyr  Gly  Met AAA GTT TTC TTC TGX TCT GTA ATA AAA TAA CGX CGX CA  GAA CGX TTA TGG GAT TAT GGX ATG
        G   C   T   T      GCC G   G   G   G           G AGA   G           C   C
                           G                             G CTX
                           A
                  PROBE 2-20mer (512)      PROBE 1-20mer (384)        PROBE 3 - 24mer (1152)
                    20 - 55z GC              30 - 60z GC                 38 - 63z GC
                    Tm = 48 - 62° C.         Tm = 52 - 64° C.            (Tm = 66 - 78° C.
```

PROBE 4 - 48mer (256)

For the 52.5 kd protein, which, as shown below, is derived from the 92.5 kd protein, the following amino acid sequence at the N-terminus was determined:

```
 1   2    3    4    5    6    7    8    9   10   11   12   13
Ala Thr  Arg  Arg  Tyr  Tyr  Leu  Gly  Ala  Val  Glu  Leu  Ser 14  15   16   17   18   19   20   21   22   23   24   25   26
Trp Asp  Tyr  Met  Gln  Set  Asp   ?   Gly  Glu  Leu  Pro
Val
```

Based on the amino acid sequence for the 52.5 kd peptide, a partially degenerate probe having the following nucleotide sequence (coding) was synthesized:

```
5'-GCA ACT AGA AGA TAT TAT TTG GGG
       A   G   G           A   A
   GCA GTT GAA TTG TCA TGG GAT TAT-3'
       A           A   T
```

This probe is useful for screening both genomic and cDNA libraries.

The amino acid sequences of two peptides obtained by digestion of the 77–80 kd doublet with endoproteinase LysC (Boehringer-Mannheim) were determined. The digestion was performed as follows. The 77–80 kd doublet was electrophoresed on an acrylamide protein gel and bands corresponding to the doublet were electroeluted. The separated material was purified and digested with endoproteinase LsyC, and the resulting peptides were separated by reverse phase HPLC. The fractions corresponding to peaks of absorbance at 280 nm were sequenced using an automated sequencer (Applied Biosystems, Foster City, Calif., Model A70A). The first sequence was as follows:

```
 1   2    3    4    5    6    7    8    9   10   11   12
Tyr Ala  Ala  Thr  Ser  Gln  Val  Leu  Leu  Pro  Ser  Lys
```

Based on this amino acid sequence, a partially degenerate probe having the following nucleotide sequence (non-coding) strand was synthesized:

```
3'-ATA CGT CGT TGA AGT GTT CAA AAC AAC GG-5'
           T   A           T   T   T
```

The second peptide had the following sequence:

```
 1   2    3    4    5    6    7    8    9   10
Val Thr  Gly  Val  Thr  Thr  Gln  Gly  Val  Lys
```

Based on this amino acid sequence, a partially degenerate probe having the following nucleotide sequence (non-coding) was prepared:

```
3'-CAA TGA CCT CAA TGA
     T   T      T   T

TGA GTT CCT CAA TTT-5'
     T           T
```

The 77/80 kd doublet was also digested with trypsin. The doublet material was purified as described for digestion with endoproteinase LysC, above, lysines were blocked by citraconylation to allow digestion only at arginines. Citraconylation was performed by suspending the proteins in a denaturing buffer, reducing and carboxymethylating the suspended proteins, and treating with citraconic anhydride while maintaining a pH between 8.5 and 9.0. After citraconylation, the proteins were digested with trypsin, and the resulting peptides separated by reverse phase HPLC. The fractions corresponding to peaks of absorbance at 280 nm were sequenced, as above. The sequence was as follows:

```
  1   2   3   4   5   6   7   8   9   10  11  12
 Met Gly Val Leu Gly Cys Glu Ala Gln Asp Leu Tyr
```

Based on this amino acid sequence, a partially degenerate probe having the following nucleotide sequence (non-coding) was synthesized:

```
3'-TAC CTT CAA AAC CCT ACG CTT CGT GTT CTA AAC
     T   T                                 T
ATA-5'
```

When procedures to determine the N-terminus sequences of the 80 and 77 Kd species were carried out, it was found that their amino termini were blocked. Therefore, the N-termini sequence was determined from material obtained by an alternative purification method which included immunoaffinity chromatography and ion exchange chromatography and precluded the use of preparative SDS-polyacrylamide gel electrophoresis. Purification of the 80/77 Kd doublet involved application of Factor VIIIC concentrate to a monoclonal antibody column followed by chromatography on a mono S cation exchanger. This material had an unblocked N-termini, indicating that the blockage detected in gel purified 80/77 Kd was an artifact resulting from the gel electrophoresis. The amino termini sequences determined for both 80 and 77 Kd species is the following (indicated with a bar in Appendix B):

```
  1   2   3   4   5   6   7   8   9   10
 Glu Ile Thr  ?   ?  Leu Gln  ?  Asp 11  12  13  14  15  16
 Gln Glu Glu Ile Asp Tyr
```

E. Amino Acid Composition

The amino acid compositions for the 77/80 kd peptides were determined by standard methods to be as follows:

| Amino Acid | 80K | 77K |
|---|---|---|
| Asp | 58 | 54 |
| Glu | 74 | 76 |
| Cys | 12 | 14 |
| Ser | 47 | 44 |

-continued

| Amino Acid | 80K | 77K |
|---|---|---|
| Gly | 51 | 46 |
| His | 8 | 12 |
| Arg | 32 | 29 |
| Thr | 35 | 29 |
| Ala | 35 | 33 |
| Pro | 33 | 30 |
| Tyr | 25 | 25 |
| Val | 46 | 44 |
| Met | 17 | 17 |
| Ile | 33 | 35 |
| Leu | 49 | 48 |
| Phe | 32 | 31 |
| Lys | 47 | 41 |
| Total No. Amino Acids | 634 | 608 |
| Calculated Molecular Weight: | 82K | 79K |

F. Preparation of Human 4× Genomic Library

Approximately 3 mg of DNA were prepared from cell culture lysates of GM1416 cells (human lymphoblastoid cell line containing 4 copies of the X chromosome).

This DNA was partially digested with the restriction enzyme Sau3A, and the digested DNA (400–500 μg) fractionated on 10%–40% sucrose gradients. Fractions in the size range 10–25 kilobases were pooled, dialyzed into Tris-EDTA and purified over Schliecher and Scheull Elutip-d sterile disposable columns. Aliquots of this DNA were ligated to EMBL-4 arms, obtained after digestion with BamHI and SalI and isolation on a gradient, and then packaged into bacteriophage lambda with an efficiency of $1 \times 10^6$ pfu/μg of insert DNA. The vector used, EMBL-4, is a modified form of bacteriophage lambda (see Karn et al., Methods Enzymol. (1983) 101:3–19). The total library consisted of $5 \times 10^6$ phage.

G. Plating and Screening of Human 4× Genomic Library

Bacteriophage were adsorbed to E. coli strain DP50 and 20 plates were plated at 50,000 pfu per plate, (150×15 mm size) to give $1 \times 10^6$ pfu total. (Details of techniques for plates, top agar, adsorption and plating are found in Molecular Cloning, A Laboratory Manual, by T. Maniatis, E. F. Fritsch and J. Sambrook; Cold Spring Harbor Lab, New York, 1982.)

Nitrocellulose filters were applied to the surface of each plate containing phage plaques (so that molecules of unpackaged phage DNA are transferred to the filters) in duplicate, and hybridized with $^{32}$P-labeled 256-fold degenerate 48-mer probe DNA (probe #4). (Details of the nitrocellulose transfer technique are found in Maniatis et al., supra.) Pre-hybridization and hybridization were carried out in Wallace mix which contains in one liter: 310 ml of distilled $H_2O$, 200 ml 50% dextran sulfate, 180 ml 1M Tris-HCl, pH 8.0, 225 ml 4M NaCl, 20 ml 0.25M EDTA, 50 ml 100× Denhardt's solution, 5 ml 100% NP-40 and 10 ml 10% SDS.

The probe was labeled by enzymatic transfer of $^{32}PO_4$ from γ-ATP$^{32}$ to the 5' phosphate end of each probe DNA molecule, catalysed by T4 polynucleotide kinase. The hybridization conditions were as follows: 10 ml hybridization mix/filter×5000 cpm of labeled probe #4/degeneracy/ml. Hybridization was carried out at 37° C. overnight. Filters were washed in 6×SSC, 1 mM EDTA at 50–55° C., air dried and used to expose X-ray film.

H. Characterization of Positive Clones

Twenty-three plaques giving positive signals for the first round of screening were replated, phage DNA transferred to nitrocellulose and hybridized with freshly labeled probe #4 (secondaries). Eleven plaques giving positive signals were replated, phage DNA transferred to nitrocellulose and hybridized with freshly labeled probe #4 (tertiaries). Eight plaques giving positive signals were isolated and DNA prepared (100 ml liquid cultures for each). The DNA corresponding to each of these 8 clones was digested with EcoRI (to release inserted human genomic DNA from the lambda vector DNA) and the resulting fragments separated by size using electrophoresis on a 0.8% agarose gel, denatured and transferred to nitrocellulose. This was done in quadruplicate and each filter hybridized with $^{32}$P-labeled probe #'s 1, 2, 3 or 4. The filters were used to expose to X-ray film and a single band of about 4.4 kb in size was found to hybridize with all four probes for two clones. These two clones were identical except that one had more insert DNA than the other (clone designations are 23 D for the larger insert of 15.21 kb and 11 for the smaller insert of approximately 13 kb). The 4.4 kb gel isolated EcoRI fragment was subcloned in vectors M13 and pUC-9 (a derivative of pBR322). DNA sequencing by the dideoxy technique on M13 DNA using the synthetic probe #3 and its reverse complement as primers was carried out.

The 4.4 kb fragment was partially sequenced and has the following sequence encompassing the probe #4 sequence, indicated in parenthesis, and the partial amino acid sequence of the 67/70 kd fragment originally determined, indicated in brackets.

```
            1                                                      10
            val ser phe   phe arg ala gln arg   glu   arg leu ser gly asn
         GG GTG TCC TTC   TTC AGG GCT CAG AGG   GAG   CGA TTA AGT GGC AAC 20
            glu ala asn arg   pro gly lys leu pro   phe   leu arg val ala thr
            GAA GCA AAC AGG   CCT GGA AAA CTT CCC   TTT   CTG AGA GTA GCA ACA 30                                                      40
            glu thr leu gln   arg leu pro pro ser   tyr   tre ile leu leu leu
            GAA ACT CTG CAA   AGA CTC CCT CCA AGC   TAT   TGG ATC CTC TTG CTT 50
            gly ile pro leu   trp tyr ser glu tyr   gln   lys lys ser gly lys
            GGG ATA CCA CTA   TGG TAC TCA GAG TAC   CAA   AAG AAG AGT GGA AAG 60                                                      70
            ser gln glu lys   ser pro glu lys thr   ala   phe lys lys lys asp
            TCC CAA GAG AAG   TCA CCA GAA AAA ACA   GCA   TTT AAG AAA AAG GAT 80
            thr ile leu ser   leu asn ala cys glu   ser   asn his ala ile ala
            ACC ATT TTG TCC   CTG AAC GCT TGT GAA   AGC   AAT CAT GCA ATA GCA 90                                                      100
            ala ile asn glu   gly gln asn lys pro   glu   ile glu val thr trp
            GCA ATA AAT GAG   GGA CAA AAT AAG CCC   GAA   ATA GAA GTC ACC TGG 110
            ala lys gln asn   arg thr glu arg leu   cys   ser gln asn pro pr
            GCA AAG CAA AAT   AGG ACT GAA AGG CTG   TGC   TCT CAA AAC CCA CCA 120                                                     130
            val leu lys arg   his gln arg glu ile   thr   arg thr thr leu gln
            GTC TTG AAA CGC   CAT CAA CGG GAA ATA   ACT   CGT ACT ACT CTT CAG 140
            ser asp gln glu   glu ile asp tyr asp   asp   thr ile ser val glu
            TCA GAT CAA GAG   GAA ATT GAC TAT GAT   GAT   ACC ATA TCA GTT GAA 150                                                     160
            met lys lys glu   asp phe asp ile tyr   asp   glu asp glu asn gln
            ATG AAG AAG GAA   GAT TTT GAC ATT TAT   GAT   GAG GAT GAA AAT CAG 170
            ser pro arg ser [ phe gln lys lys thr ( arg   his tyr phe ile ala
            AGC CCC CGC AGC   TTT CAA AAG AAA ACA   CGA   CAC TAT TTT ATT GCT 180                                                     190
            ala val glu arg   leu trp asp tyr gly   met )  ser ser ser pro his
            GCA GTG GAG AGG   CTC TGG GAT TAT GGG   ATG /] AGT AGC TCC CCA CAT 200
            val leu arg asn   arg tyr glu cys ile   gly   tyr ser phe ala leu
            GTT CTA AGA AAC   AGG TAT GAA TGC ATT   GGT   TAT TCC TTT GCT CTG 210 211
            leu leu OP
            CTC TTG TGA CAT   TTGACTTTACCAGATGATG   ACA   CCAACC
```

This clone thus corresponds to the gene for the 77/80 kd doublet protein, which, as it has been shown above, corresponds in part to the human Factor VIIIC complex.

Clone 23D was subcloned in phage M13 as EcoRI fragments, and the sequence corresponding to the inserted human DNA was determined. The complete 15.155 kb sequence of clone 23D sequence is set forth in Appendix A, attached hereto. The subclone designations are given at the right hand margin of the sequence, and refer to the EcoRI—EcoRI fragment extending in the $3^1$-direction. An open reading frame of 3.110 kb was found to exist from the 3'-end of the 70-3 fragment to the middle of the 4.4 kb fragment. The open reading frame thus comprises at least part of the coding region for the 77/80 kb doublet protein.

coding sequence can be inserted into a plasmid, e.g., pBR322, into which has been inserted the long terminal repeats of Maloney murine sarcoma virus, so that the Clone 23 or 11 sequences are under the transcriptional control of the viral regulatory system. The constructs may then be introduced into 3T3 mouse fibroblasts for efficient expression (see Perkins et al., *Molecular and Cellular Biology*, June 1983, Vol. 3, No. 6, p. 1123).

(2) Further 3' cDNA Region Construction

An oligo-dT-primed cDNA library was prepared from human kidney poly A+ RNA using the primer adapter method. Briefly, poly $A^+$ RNA isolated from human kidney was primed at the 3' end of the mRNA using a primer (F-1) having the following sequence:

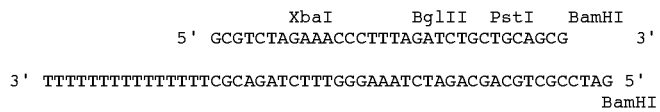

I. Preparation of Full-length cDNA Clones (1) Initial Constructions

Three cDNA clones encoding portions of Factor VIIIC were obtained as follows. Clone C1 was obtained by screening a human liver cDNA library with a probe constructed from the 4.4 kb EcoRI fragment of clone 23 D. Clone C2 was also obtained by screening a human liver cDNA library with the 4.4 kb probe. Clone 2–11 was obtained by screening a human kidney cDNA library with a synthetic 45-mer probe based on the DNA sequence found at the 3'-end of the open reading frame of clone 23 D (nucleotides 9391 to 9435 in Appendix A). The probe comprised the non-coding strand of the following sequence:

```
                Ser Pro Arg Ser Phe Gln Lys Lys
Non-coding-   5'-AGC CCC CGC AGC TTT CAA AAG AAA
 (probe)      3'-TCG GGG GCG TCG AAA GTT TTC TTT Thr Arg His Tyr Phe Ile Ala
              ACA CGA CAC TAT TTT ATT GCT-3'
              TGT GCT GTG ATA AAA TAA CGA-5'
```

The clones were sequenced and their locations relative to the genomic DNA of clone 23 D determined by comparing the sequences. Clone C1, which is 304 kp in length, overlaps with the open reading frame from nucleotide 7773 to 8077, as numbered in Appendix A. Clone C2, which is 878 bp in length, partially overlaps with the 3'-end of the open reading frame beginning at nucleotide 9538 and extending beyond nucleotide 9497 which is at the 3'-end of the open reading frame. Clone 2–11, which is 572 bp in length, also overlaps the 3'-end of the open reading frame beginning at nucleotide 9190 and extends beyond its termination. These findings thus confirm that the open reading frame is transcribed.

The coding information derived from the 4.4 kb open reading frame may be combined with the additional coding information derived from clones 2–11 and C2 to provide a 3.854 kb coding sequence containing all but about 4 kb of the full coding sequence (See, Appendix B). The regions corresponding to the C1, C2 and 2–11 probes are boxed.

To prepare Factor VIIIC fragments, the DNA sequences from Clone 23 or Clone 11 are inserted into an SV-40 promoter as described by Laub et al., *J. Virology* (1983) 48:271, so as to be under the control of the SV-40 early promoter. The resulting recombinant plasmid may be transfected into COS cells (Guzman, supra.). Alternatively, the single-stranded cDNA was synthesized and size-selected on denaturing agarose-methyl mercury gels to isolate fragments greater than 2 kb. The cDNA fragments were eluted, C-tailed, annealed to adapters and placed in a pUC9 vector (Pharmacia Fine Chemicals, Piscataway, N.Y.), ligated, repaired using T4 DNA polymerase and finally transformed into *E. coli* MC1061. Approximately 500,000 clones were obtained.

This library was divided into 20 pools and analyzed by Southern hybridization after digestion with PstI, using the 4.3 kb EcoRI genomic fragment described previously as a probe. In one of the pools, pool 1–7, a clone was found to contain fragments hybridizing to the genomic probe.

Further PstI digestion of the clone yielded two fragments of about 1350 and 600 bp that hybridized to the 4.3 kb EcoRI probe. Hybridization of a 600 bp fragment was expected based on the sequence of the 4.3 kb fragment. Upon probing with a piece of the 3' end of the C2-cDNA described previously, a new 1200 bp fragment was located by hybridization. However, only the 600 bp fragment hybridized to a separate piece from the 5' end of the C2-cDNA. Based on this information, it was believed that the 5 kb cDNA clone encompassed more than the entire 3' half of the human Factor VIIIC precursor protein coding region.

To minimize stability problems experienced after plating with high-efficiency $rec^+$ bacteria on large inserts, DNA from pool 1–7 was digested with XmaI (which linearizes the positive plasmid), run on a low melting agarose gel, and one region corresponding to a molecular weight of about 7.5 kb was excised. This DNA was extracted from the agarose, recircularized with DNA ligase and subsequently used to transform bacteria. Approximately 25,000 colonies were plated and reanalyzed by colony hybridization to the 4.3 kb EcoRI fragment. Two positive colonies were obtained and, for high purity, isolated by two further cycles of plating hybridization. The resultant clone, designated pF8-100, contains an insert of about 5,000 bp, which after digestion with PstI gives five fragments of approximately 1600, 1350, 1200, 600 and 200 bp. Utilizing the M-13 dideoxy method, the 5 kb cDNA insert has been completely sequenced, as shown in FIG. 1.* The insert contains the last 60% of the coding region and substantially all of the 3' untranslated region of the human kidney messenger RNA for Factor VIIIC.

(3) Further 5' cDNA Region Construction

To obtain the 5' region of human Factor VIIIC cDNA, approximately 1×10⁶ clones with an average insert size of about 3 kb were obtained from a total of four independent transformation experiments utilizing a cDNA library constructed as described previously using the F-1 primer, but in addition using a second primer (303) that has the following sequence located near a BglII site of the pF8-100 cDNA clone:

```
5' CCATTACTCAGTCTCCCTTATCAGATTGCCTTACGAGGAG 3'
3' TAGTCTAACGGAATGCTCCTCCTAG 5'.
```

For initial screening, the transformant pools were linearized with SmaI and produced a broad DNA band in the 5 to 7 kb region on the gels. For further screening, the library was divided into 16 pools and the DNA analyzed by Southern hybridization, probing with the 4.3 kb EcoRI fragment. Of the first four pools analyzed, two showed the presence of a hybridizing band in the 6.5 to 7 kb range, the size expected for the total of the base pairs in the vector plus the base pairs of the Factor VIIIC cDNA extending from the site of internal priming to the 5' end (about 4 kb).

To confirm that the positive pools contained the 5' end cDNA sequences coding for human Factor VIIIC cDNA, cDNA inserts from the pools was digested with SmaI and SacI, which should cut the cDNA into two pieces of approximately 1 and 3 kb. When the fragments were analyzed by Southern hybridization using the 4.3 kb EcoRI fragment as a probe, as expected, the two fragments hybridized—indicating that this insert contained the 5' region of the Factor VIIIC cDNA.

For isolation of a single cDNA clone, approximately 200,000 transformants from one of the positive pools were plated, lifted onto nitrocellulose filters and hybridized to nick-translated 4.3 kb EcoRI probes. Six double positive colonies were obtained, two of which were isolated as single colonies by replating. One of these clones was a 3.8 kb insert designated pF8-103, which contained the 3' end of the Factor VIIIC cDNA; while the other clone of about 4 kb, designated pF8-102, was isolated and subjected to further analysis.

The pF8-102 cDNA insert was digested with HindIII, PstI, SstI (SacI), EcoRI, BamHI, FPHI, BglII and SmaI. It was also cloned in M13. Sequence was obtained from the universal primer, as well as internally, using various specific synthetic primers. The sequence obtained is presented in FIG. 1, which together with the sequence for pF8-100, provide a cDNA encoding the entire human Factor VIIIC coding region.

(4) Full-Length cDNA Assembly

Details of the assembly of a full-length cDNA for expression in mammalian cells is shown in FIG. 2. The lack of convenient restriction sites in the pF8-100 and pF8-102 overlap region required the use of DNA fragments derived from the 4.3 kb EcoRI genomic fragment as well. Plasmid pF8/4.5 contains the 4.3 kb EcoRI fragment clone in pUC9.

Briefly, pF8-100 was cut with SmaI and AbaI, and a 4.8 kb fragment was isolated by gel electrophoresis. Likewise, a 1.7 kb fragment was obtained from pF8/4.5 by digestion with AbaI and EcoRI. These two fragments were ligated into open pUC9 (cleaved with SmaI and EcoRI) to yield a plasmid designated pF8/6.5. Cutting this plasmid with SacI and SalI yielded a 6.5 kb fragment (Fragment 1). A second fragment (Fragment 2) was obtained by cutting pF8-102 with SacI, which upon gel isolation yielded a 3 kb piece.

Fragments 1 and 2 were subsequently ligated into a modified vector pSV7d to yield expression plasmid pSVF8-200, which is capable of expressing human Factor VIIIC protein.

The plasmid pSV7d was constructed as follows: the 400 bp BamHI/HindIII fragment containing the SV40 origin of replication and early promoter was excised from pSVgtI (Mulligan, R. et al., *J. Mol. Cell Biol.* (1981) 1:8.54–864) and purified. The 240 bp SV40 BclI/BamHI fragment containing the SV40 poly A addition site was excised from pSV2/dhfr (Subramani et al., *J. Mol. Cell Biol.* (1981) 1:854–864) and purified. The fragments were fused through the following linker:

```
                      Stop Codons
                      1    2    3

5'-AGCTAGATCTCCCGGGTCTAGATAAGTAAT-3'
      TCTAGAGGGCCCAGATCTATTCATTACTAG

HindIII  BglII SmaI  XbaI      BclI overhang.
```

This linker contains five restriction sites, as well as stop codons in all three reading frames. The resulting 670 bp fragment (containing the SV40 origin of replication, the SV40 early promoter, the polylinker with stop codons and the SV40 polyadenylation site) was cloned into the BamHI site of pML, a pBR322 derivative with about a 1.5 kb deletion (Lusky and Botchan, *Cell* (1984) 36:391), to yield pSV6. The EcoRI and EcoRV sites in the pML sequences of pSV6 were eliminated by digestion with EcoRI and EcoRV, treated with Bal31 nuclease to remove about 200 bp on each end, and finally religated to yield pSV7a. The Bal31 resection also eliminated one BamHI restriction site flanking the SV40 region, approximately 200 bp away from the EcoRV site. To eliminate the second BamHI site flanking the SV40 region, pSV7a was digested with NruI, which cuts in the pML sequence upstream from the origin of replication. This was recircularized by blunt end ligation to yield pSV7b.

pSV7c and pSV7d represent successive polylinker replacements. Firstly, pSV7b was digested with StuI and XbaI. Then, the following linker was ligated into the vector to yield pSV7c:

```
          BglII EcoRI   SmaI    KpnI XbaI

5'-AGATCTCGAATTCCCCGGGGTACCT
         TCTAGAGCTTAAGGGGCCCCATGGAGATC
```

Thereafter, pSV7c was digested with BglII and XbaI, and then ligated with the following linker to yield pSV7d:

```
      BglII EcoRI    SmaI XbaI   BamHI SalI

5'-GATCTCGAATTCCCCGGGTCTAGAGGATCCGTCGAC
            AGCTTAAGGGGCCCAGATCTCCTAGGCACGTGATC
```

Plasmid pSV7d was digested with BamHI to cut in the polylinker region downstream of the SV40 early promoter. The following 49 bp BamHI-SacI linker adaptor, which codes for the last 30 bp of untranslated region and the first 15 bp of the human Factor VIIIC coding sequence, was chemically synthesized and ligated to pSV7d:

```
        -35      -30   -25   -20   -15   -10   -5       met gln ile glu
5' GATCC TCTCC AGTTG AACAT TTGTA GCAAT AAGTC ATG CAA ATA GAG CT 3'

BamHI₃,G AGAGG TCAAC TTGTA AACAT CGTTA TTCAG TAC GTT TATC SacI 5'
```

This ligated plasmid was subsequently digested with SacI to remove excess linkers and with SalI to provide a SalI overhang.

Fragment 1, the 2.9 kb SacI fragment from pF9-102 containing the 5' coding region of human Factor VIIIC, and Fragment 2, the 6.5 kb SacI-SalI fragment from pF8-6.5 which contains the 3' coding region of the factor, and pSV7d modified vector containing the linker adaptor were ligated together. This ligation mix was then used to transform *E. coli* HB101, and colonies were selected by resistance to ampicillin.

300 transformants were screened by colony filter hybridization using the BamHI-SacI 5' adaptor or the 2.9 kb SacI fragment as probes. Those colonies positive with both probes were then analyzed by restriction mapping. Plasmid pSVF8-200, which contains the entire coding region for the human Factor VIIIC gene and a 5' untranslated region properly fused in transcriptional orientation to the SV40 early promoter, was obtained.

(5) Transfections and Assays

Utilizing the chloroquine diphosphate transfection method (Luthman and Magnuson (1983) *Nucl. Acid. Res.*, 11:1295–1308), Cos-7 cells growing in 4 cm² slide wells were transfected with 0.5 micrograms of pSVF8-200 in the presence of calcium. At 40, 48 and 60 hours post-transfection, cell culture media was removed and tested for human factor VIIIC activity using the coagulation assay described previously (General Diagnostics, Inc.). The cells remaining on the slides were fixed with methanol for indirect immune fluorescence studies.

The fixed slides were stained with six different antibodies against human Factor VIIIC and a second antibody labeled with FITC (Cappel Labs). The partial results are shown in the following table:

TABLE I

| 1st Antibody | Goat 2nd Antibody Conjugation with FITC | Results |
|---|---|---|
| 1. Hybritech monoclonal anti-FVIIIC | anti-mouse | (+/−) All FVIII:C cells |
| 2. Synbiotic monoclonal anti-FVIIIC (80 kd specific) | anti-mouse | looked slightly more positive |
| 3. Monoclonal #56 anti FVIIIC (Nordisk) | anti-mouse | than negative controls |
| 4. Human polyclonal inhibitory serum (HZ) (Nordisk) | anti-human | (+) Low background and bright FVIII:C positive cells |
| 5. Rabbit polyclonal against 92 kd (Chiron) | anti-rabbit | (−) Both control and transfected cells show low fluorescence |
| 6. Rabbit polyclonal against 80 kd (Nordisk) | anti-rabbit | (+) Clear FVIII:C positives seen with 48 hr. cells |

The human polyclonal showed positive immunofluorescent cells at 48 and 60 hours post-transfection. The 80 kd rabbit polyclonal showed positive cells at 48 hours post-transfection. All other antibodies gave high backgrounds, rendering accurate determinations impractical.

The production of active human Factor VIIIC by the transfected Cos cells was detected using the previously described commercially available kit coagulation assay (General Diagnostics, Inc.). However, it was found that Cos cell medium interfered with the coagulation assay by indicating apparent coagulation activity equal to about 0.05 units per ml. This apparent activity is probably caused by a serum component present in the medium. Cos cell conditioned medium gave about the same apparent activity as fresh medium, i.e., medium that had not been used for growing cells.

To correct for the apparent activity of the Cos cell medium, a revised standard curve was established using serial dilutions of a purified Factor VIIIC preparation (purified from cryoprecipitate, as previously described) diluted in Cos cell conditioned medium with serum. Supernatants from Cos cells transformed with the plasmid pSV8-200 were then assayed for clotting activity. As shown in Table II, samples taken at 40 hours post-transformation, and frozen immediately at −70° C. until assay, had about 0.045 units per ml activity, the 48 hour sample had about 0.055 units per ml activity, while the 60 hour sample had about 0.07 units per ml activity.

TABLE II

Detection of Coagulation Activity in COS Cells Transformed with Factor VIII:C Gene

| Sample | Coagulation Time (sec.) | Activity (units/ml) |
|---|---|---|
| Purified FVIII preparation 1:5,000 dilution | 35.9 | 0.23$^x$ |
| Purified FVIII preparation 1:10,000 dilution | 48.4 | 0.11$^x$ |
| Purified FVIII preparation 1:20,000 dilution | 55.9 | 0.058$^x$ |
| Purified FVIII preparation 1:40,000 dilution | 67.9 | 0.028$^x$ |
| 40 hr sample | | |
| 2a | 58.9 | 0.049$^y$ |
| 2b | 61.9 | 0.041$^y$ |
| 48 hr sample | | |
| 1a | 58.2 | 0.051$^y$ |
| 1b | 56.9 | 0.057$^y$ |
| 60 hr sample | | |
| 1a | 52.4 | 0.086$^y$ |
| 1b | 56.4 | 0.060$^y$ |

$^x$Activity calculated from normal standard curve using the same dilutions of FVIII in coagulation buffer rather than COS cell conditioned medium.
$^y$Activity calculated from modified standard curve using COS cell conditioned medium as a diluent.

To confirm that the coagulation activity detected in the Cos cells/Factor VIIIC transfectant media was due to active Factor VIIIC protein sequences, the media was preincubated with an inhibitory human polyclonal anti-Factor VIIIC antibody (HZ antibody, Nordisk) known to specifically inhibit Factor VIIIC activity. The coagulation assay was performed essentially as detailed above, but each sample was pre-incubated with the antibodies for about 2 hr. at 37° C. The assay results are shown in Table III.

TABLE III

| Media | Pre-incubation[a] | Antibody | Dilution[b] | Coagulation Time (sec.) |
|---|---|---|---|---|
| COS cell | − | — | — | 108.9 |
| COS cell/pSVF8-200 | − | — | — | 83.4 |
| COS cell/pSVF8-200 | + | — | — | 84.4 |
| COS cell/pSVF8-200 | + | F3A/B | 1/100 | 81.9 |
| COS cell/pSVF8-200 | + | HZ IgG | 1/100 | 110 |
| COS cell/pSVF8-200 | + | HZ IgG | 1/500 | 105.4 |
| COS cell/pSVF8-200 | + | HZ IgG | 1/1,000 | 103.9 |
| COS cell/pSVF8-200 | + | HZ IgG | 1/10,000 | 98.4 |

[a]Incubation was for 2 h at 37° C.
[b]Dilutions were made in coagulation buffer.

As shown in Table III, the COS cell/FVIII:C media clearly has an accelerated clotting time compared to the COS cell media alone. Preincubation of this media for 2 h at 37° C. did not prolong the clotting time nor did preincubation in the presence of a monoclonal antibody directed against a major herpes simplex glycoprotein (F3A/B). However, preincubation with various concentrations of human inhibitor serum (HZ IgG) clearly retarded the coagulation time, approximately equal to that of the control reaction. These results confirm that transfected COS cells produce and secrete active FVIIIC protein.

The above results also demonstrate that genomic DNA sequences have been isolated which code for portions of the Factor VIIIC protein. By use of this genomic DNA, the DNA may be further manipulated to provide for a sequence encoding for Factor VIIIC complex subunits. The DNA may then be used in an expression vector for production of the Factor VIIIC, which may be used in a variety of ways, for example, as reagents in diagnostic assays, as therapeutic agents, for the production of monoclonal or polyclonal antibodies, which may then be used for the purification of Factor VIIIC complex or other purposes. The genomic DNA sequences may also be used for isolation of mRNA encoding proFactor VIIIC to provide for the precursor protein. This protein may then be administered in vivo for various therapeutic purposes.

Although the foregoing invention has been described in some detail by way of illustration and example for purposes of clarity of understanding, it will be obvious that certain changes and modifications may be practiced within the scope of the appended claims.

What is claimed is:

1. A purified nucleic acid molecule comprising a nucleotide sequence encoding at least a portion of human Factor VIII:C, wherein the portion of human Factor VIII:C is the amino acid sequence PHE-GLN-LYS-LYS-THR-ARG-HIS-TYR-PHE-ILE-ALA-ALA-VAL-GLU-ARG-LEU-TRP-ASP-TYR-GLY-MET.

2. The purified nucleic acid molecule of claim 1, wherein the nucleic acid is DNA.

3. The purified nucleic acid molecule of claim 1, wherein the nucleotide sequence encoding said amino acid sequence is TTT CAA AAG AAA ACA CGA CAC TAT TTT ATT GCT GCA GTG GAG AGG CTC TGG GAT TAT GGG ATG.

4. The purified nucleic acid molecule of claim 3, comprising the expressed nucleotide sequence of the 14.43 kb EcoRI fragment of the human genomic Factor VIII:C DNA insert of bacteriophage λFVIII23D.

5. The purified nucleic acid molecule of claim 3, comprising the expressed nucleotide sequence of the 4.3 kb EcoRI fragment of the human genomic Factor VIII:C DNA insert of bacteriophage λFVIII23D.

6. A purified nucleic acid molecule, wherein the nucleic acid molecule encodes ARG-HIS-TYR-PHE-ILE-ALA-ALA-VAL-GLU-ARG-LEU-TRP-ASP-TYR-GLY-MET and hybridizes to at least one oligonucleotide of the 256-fold degenerate probe

```
3' TCT GTA ATG AAA TAG CGA CGA CAC CTT TCT
     C   G       G       G           C   C

GAC ACC CTA ATG CCG TAC 5'
``` at 37° C. in a hybridization mixture containing 310 ml distilled $H_2O$, 220 ml 50% dextran sulfate, 180 ml 1 M Tris HCl, pH 8.0, 225 ml 4 M NaCl, 20 ml 0.25 M EDTA, 50 ml 100× Denhardt's solution, 5 ml 100% NP-40, and 10 ml 10% SDS.

7. A vector comprising a purified nucleic acid molecule comprising a nucleotide sequence encoding at least a portion of human Factor VIII:C, wherein the portion of human Factor VIII:C is the amino acid sequence PHE-GLN-LYS-LYS-THR-ARG-HIS-TYR-PHE-ILE-ALA-ALA-VAL-GLU-ARG-LEU-TRP-ASP-TYR-GLY-MET.

8. The vector of claim 7, wherein the nucleic acid is DNA.

9. The vector of claim 7, wherein the nucleotide sequence encoding said amino acid sequence is TTT CAA AAG AAA ACA CGA CAC TAT TTT ATT GCT GCA GTG GAG AGG CTC TGG GAT TAT GGG ATG.

10. The vector of claim 7, 8, or 9, wherein the vector is an expression vector.

11. The vector of claim 10, wherein said vector is a recombinant mammalian virus.

12. A host cell composition prepared by introducing into a host cell a purified nucleic acid molecule comprising a nucleotide sequence encoding at least a portion of human Factor VIII:C, wherein the portion of human Factor VIII:C is the amino acid sequence PHE-GLN-LYS-LYS-THR-ARG-HIS-TYR-PHE-ILE-ALA-ALA-VAL-GLU-ARG-LEU-TRP-ASP-TYR-GLY-MET to provide a recombinant host cell, and growing said host cell to provide said host cell composition.

13. The host cell composition of claim 12, wherein the nucleic acid molecule is DNA.

14. The host cell composition of claim 12, wherein the nucleic acid molecule comprises the nucleotide sequence TTT CAA AAG AAA ACA CGA CAC TAT TTT ATT GCT GCA GTG GAG AGG CTC TGG GAT TAT GGG ATG.

15. The host cell composition of claim 12, 13 or 14, wherein the nucleic acid is a vector.

16. The host cell composition of claim 15, wherein the vector is an expression vector.

17. The host cell composition of claim 12, wherein the host cell is a mammalian cell.

18. The host cell composition of claim 12, wherein the host cell is *E. coli*.

19. A method of preparing a recombinant DNA vector, comprising:
   (a) providing a DNA molecule comprising a nucleotide sequence encoding the amino acid sequence ARG-HIS-TYR-PHE-ILE-ALA-ALA-VAL-GLU-ARG-LEU-TRP-ASP-TYR-GLY-MET;
   (b) providing a DNA vector;
   (c) inserting said DNA molecule into said DNA vector to provide the recombinant DNA vector.

20. The method of claim 19, wherein the nucleotide sequence encoding the amino acid sequence ARG-HIS- TYR-PHE-ILE-ALA-ALA-VAL-GLU-ARG-LEU-TRP-ASP-TYR-GLY-MET is CGA CAC TAT TTT ATT GCT GCA GTG GAG AGG CTC TGG GAT TAT GGG ATG.

21. The method of claim 19 or 20, further comprising introducing said recombinant DNA vector into a host cell.

22. The method of claim 21, further comprising growing said host cell into which said recombinant vector has been introduced to provide a composition of host cells comprising said recombinant vector.

23. A method for producing a polypeptide comprising an amino acid sequence PHE-GLN-LYS-LYS-THR-ARG-HIS-TYR-PHE-ILE-ALA-ALA-VAL-GLU-ARG-LEU-TRP-ASP-TYR-GLY-MET, comprising introducing into a host cell a purified nucleic acid molecule comprising a nucleotide sequence encoding the amino acid sequence.

24. The method of claim 23, wherein the purified nucleic acid molecule is DNA.

25. The method of claim 24 wherein the DNA encoding the amino acid sequence is TTT CAA AAG AAA ACA CGA CAC TAT TTT ATT GCT GCA GTG GAG AGG CTC TGG GAT TAT GGG ATG.

26. A purified nucleic acid molecule comprising a nucleotide sequence encoding PHE-GLN-LYS-LYS-THR-ARG-HIS-TYR-PHE-ILE-ALA-ALA-VAL-GLU-ARG-LEU-TRP-ASP-TYR-GLY-MET.

27. The purified nucleic acid molecule of claim 25, wherein the nucleic acid is DNA.

28. The purified nucleic acid molecule of claim 25, wherein the nucleotide sequence is TTT CAA AAG AAA ACA CGA CAC TAT TTT ATT GCT GCA GTG GAG AGG CTC TGG GAT TAT GGG ATG.

29. The purified nucleic acid molecule of claim 25, comprising the expressed nucleotide sequence of the 14.43 kb EcoRI fragment of the human genomic Factor VIII:C DNA insert of bacteriophage λFVIII23D.

30. The purified nucleic acid molecule of claim 25, comprising the expressed nucleotide sequence of the 4.3 kb EcoRI fragment of the human genomic Factor VIII:C DNA insert of bacteriophage λFVIII23D.

31. A vector comprising a purified nucleic acid molecule comprising a nucleotide sequence encoding PHE-GLN-LYS-LYS-THR-ARG-HIS-TYR-PHE-ILE-ALA-ALA-VAL-GLU-ARG-LEU-TRP-ASP-TYR-GLY-MET.

32. The vector of claim 31 wherein the nucleic acid is DNA.

33. The vector of claim 31 wherein the nucleotide sequence is TTT CAA AAG AAA ACA CGA CAC TAT TTT ATT GCT GCA GTG GAG AGG CTC TGG GAT TAT GGG ATG.

34. The vector of claim 31, 32, or 33 wherein the vector is an expression vector.

35. The vector of claim 31 wherein the vector is a recombinant mammalian virus.

36. A host cell composition prepared by introducing into a host cell a purified nucleic acid molecule comprising a nucleotide sequence encoding PHE-GLN-LYS-LYS-THR-ARG-HIS-TYR-PHE-ILE-ALA-ALA-VAL-GLU-ARG-LEU-TRP-ASP-TYR-GLY-MET, to provide a recombinant host cell, and growing the host cell to provide the host cell composition.

37. The host cell composition of claim 36 wherein the nucleic acid molecule is DNA.

38. The host cell composition of claim 36 wherein the nucleic acid molecule comprises the nucleotide sequence TTT CAA AAG AAA ACA CGA CAC TAT TTT ATT GCT GCA GTG GAG AGG CTC TGG GAT TAT GGG ATG.

39. The host cell composition of claim 36, 37, or 38 wherein the nucleic acid is a vector.

40. The host cell of claim 39 wherein the vector is an expression vector.

41. The host cell of claim 36 wherein the host cell is a mammalian cell.

42. The host cell of claim 36 wherein the host cell is *E. coli*.

43. The method of claim 23 wherein the host cell is a mammalian cell.

44. The method of claim 23 wherein the host cell is *E. coli*.

45. An isolated nucleic acid composition which comprises a nucleic acid molecule comprising (a) a nucleotide sequence with encodes PHE-GLN-LYS-LYS-THR-ARG or (b) a nucleotide sequence fully complementary to (a).

46. The composition of claim 45 wherein the nucleotide sequence encoding PHE-GLN-LYS-LYS-THR-ARG is TTT-CAA-AAG-AAA-ACA-CGA.

47. A vector comprising a nucleic acid molecule which encodes the amino acid sequence PHE-GLN-LYS-LYS-THR-ARG.

48. The vector of claim 47 wherein the nucleic acid molecule comprises TTT-CAA-AAG-AAA-ACA-CGA.

49. A host cell comprising the vector of claim 47.

50. The host cell of claim 49 wherein the nucleic acid molecule comprises TTT-CAA-AAG-AAA-ACA-CGA.

51. A method of preparing a recombinant vector comprising the step of inserting a nucleic acid molecule into a vector, wherein the nucleic acid molecule comprises a nucleotide sequence which encodes PHE-GLN-LYS-LYS-THR-ARG.

52. The method of claim 51 wherein the nucleotide sequence is TTT-CAA-AAG-AAA-ACA-CGA.

53. A method of producing a polypeptide, comprising the step of introducing into a host cell the vector of claim 49, wherein the vector encodes the polypeptide.

54. The method of claim 53 wherein the nucleotide sequence which encodes PHE-GLN-LYS-LYS-THR-ARG is TTT-CAA-AAG-AAA-ACA-CGA.

55. An isolated nucleic acid composition which comprises a nucleic acid molecule comprising (a) a nucleotide sequence which encodes GLU-ARG-LEU-TRP-ASP-TYR-GLY-MET or (b) a nucleotide sequence fully complementary to (a).

56. The composition of claim 55 wherein the nucleotide sequence which encodes GLU-ARG-LEU-TRP-ASP-TYR-GLY-MET is GAG-AGG-CTC-TGG-GAT-TAT-GGG-ATG.

57. A vector comprising a nucleic acid molecule which encodes GLU-ARG-LEU-TRP-ASP-TYR-GLY-MET.

58. The vector of claim 57 wherein the nucleic acid molecule comprises GAG-AGG-CTC-TGG-GAT-TAT-GGG-ATG.

59. A host cell comprising the vector of claim 57.

60. The host cell of claim 59 wherein the nucleic acid molecule comprises GAG-AGG-CTC-TGG-GAT-TAT-GGG-ATG.

61. A method of preparing a recombinant vector comprising the step of inserting a nucleic acid molecule into a vector, wherein the nucleic acid molecule comprises a nucleotide sequence which encodes GLU-ARG-LEU-TRP-ASP-TYR-GLY-MET.

62. The method of claim 61 wherein the nucleotide sequence is GAG-AGG-CTC-TGG-GAT-TAT-GGG-ATG.

63. A method of producing a polypeptide, comprising the step of introducing into a host cell the vector of claim 57, wherein the vector encodes the polypeptide.

64. The method of claim 63 wherein the nucleotide sequence which encodes GLU-ARG-LEU-TRP-ASP-TYR-GLY-MET is GAG-AGG-CTC-TGG-GAT-TAT-GGG-ATG.

65. An isolated nucleic acid composition which comprises a nucleic acid molecule comprising (a) a nucleotide sequence which encodes ARG-HIS-TYR-PHE-ILE-ALA-ALA-VAL-GLU-ARG-LEU-TRP-ASP-TYR-GLY-MET or (b) a nucleotide sequence fully complementary to (a).

66. The composition of claim 65 wherein the nucleotide sequence which encodes ARG-HIS-TYR-PHE-ILE-ALA-ALA-VAL-GLU-ARG-LEU-TRP-ASP-TYR-GLY-MET is CGA-CAC-TAT-TTT-ATT-GCT-GCA-GTG-GAG-AGG-CTC-TGG-GAT-TAT-GGG-ATG.

67. A vector comprising a nucleic acid molecule which encodes ARG-HIS-TYR-PHE-ILE-ALA-ALA-VAL-GLU-ARG-LEU-TRP-ASP-TYR-GLY-MET.

68. The vector of claim 67 wherein the nucleotide sequence which encodes ARG-HIS-TYR-PHE-ILE-ALA-ALA-VAL-GLU-ARG-LEU-TRP-ASP-TYR-GLY-MET is CGA-CAC-TAT-TTT-ATT-GCT-GCA-GTG-GAG-AGG-CTC-TGG-GAT-TAT-GGG-ATG.

69. A host cell comprising the vector of claim 67.

70. The host cell of claim 69 wherein the nucleotide sequence which encodes ARG-HIS-TYR-PHE-ILE-ALA-ALA-VAL-GLU-ARG-LEU-TRP-ASP-TYR-GLY-MET is CGA-CAC-TAT-TTT-ATT-GCT-GCA-GTG-GAG-AGG-CTC-TGG-GAT-TAT-GGG-ATG.

71. A method of preparing a recombinant vector comprising the step of inserting a nucleic acid molecule into a vector, wherein the nucleic acid molecule comprises a nucleotide sequence which encodes ARG-HIS-TYR-PHE-ILE-ALA-ALA-VAL-GLU-ARG-LEU-TRP-ASP-TYR-GLY-MET.

72. The method of claim 64 wherein the nucleotide sequence which encodes ARG-HIS-TYR-PHE-ILE-ALA-ALA-VAL-GLU-ARG-LEU-TRP-ASP-TYR-GLY-MET is CGA-CAC-TAT-TTT-ATT-GCT-GCA-GTG-GAG-AGG-CTC-TGG-GAT-TAT-GGG-ATG.

73. A method of producing a polypeptide, comprising the step of introducing into a host cell the vector of claim 67, wherein the vector encodes the polypeptide.

74. The method of claim 73 wherein the nucleotide sequence which encodes ARG-HIS-TYR-PHE-ILE-ALA-ALA-VAL-GLU-ARG-LEU-TRP-ASP-TYR-GLY-MET is CGA-CAC-TAT-TTT-ATT-GCT-GCA-GTG-GAG-AGG-CTC-TGG-GAT-TAT-GGG-ATG.

* * * * *

UNITED STATES PATENT AND TRADEMARK OFFICE
CERTIFICATE OF CORRECTION

PATENT NO. : 7,138,505 B1 Page 1 of 1
APPLICATION NO. : 07/569376
DATED : November 21, 2006
INVENTOR(S) : Kuo et al.

It is certified that error appears in the above-identified patent and that said Letters Patent is hereby corrected as shown below:

Title page, item (75)  Inventors: should read --George Kuo, San Francisco, CA (US);Frank Masiarz, San Francisco, CA (US); Martha Truett, Oakland, CA (US); Pablo Valenzuela, San Francisco, CA (US); Mirella Ezban Rasmussen, Copenhagen (DK)--

Signed and Sealed this

Twenty-first Day of August, 2007

JON W. DUDAS
*Director of the United States Patent and Trademark Office*